(12) United States Patent
Keaney et al.

(10) Patent No.: US 10,702,647 B2
(45) Date of Patent: Jul. 7, 2020

(54) SYSTEMS, METHODS, AND DEVICES FOR REMOVING CIRCULATING TUMOR CELLS FROM BLOOD

(71) Applicant: Viatar LLC, Lowell, MA (US)

(72) Inventors: Stephen S. Keaney, Groton, MA (US); Katherine J. Soojian, Newton, MA (US); Russell W. Bowden, Tyngsboro, MA (US); Ilan K. Reich, New York, NY (US)

(73) Assignee: Viatar LLC, Lowell, MA (US)

( * ) Notice: Subject to any disclaimer, the term of this patent is extended or adjusted under 35 U.S.C. 154(b) by 55 days.

(21) Appl. No.: 15/557,066

(22) PCT Filed: Mar. 10, 2016

(86) PCT No.: PCT/US2016/021775
§ 371 (c)(1),
(2) Date: Sep. 8, 2017

(87) PCT Pub. No.: WO2016/145198
PCT Pub. Date: Sep. 15, 2016

(65) Prior Publication Data
US 2018/0043084 A1    Feb. 15, 2018

Related U.S. Application Data

(60) Provisional application No. 62/131,075, filed on Mar. 10, 2015.

(51) Int. Cl.
*A61M 1/34* (2006.01)
*A61M 1/36* (2006.01)
(Continued)

(52) U.S. Cl.
CPC ............ *A61M 1/3635* (2014.02); *A61M 1/34* (2013.01); *A61M 1/341* (2014.02);
(Continued)

(58) Field of Classification Search
CPC .......... B01D 2201/18; B01D 2201/184; B01D 2329/1216; B01D 2325/02;
(Continued)

(56) References Cited

U.S. PATENT DOCUMENTS 5,399,265 A * 3/1995 Nehls ................... B01D 29/012
210/490
2006/0252054 A1* 11/2006 Lin ......................... A61M 1/36
435/6.11
(Continued)

FOREIGN PATENT DOCUMENTS

WO     1998029149 A1    7/1998
WO     2011119535 A1    9/2011
(Continued)

OTHER PUBLICATIONS

International Search Report and Written Opinion for International Application No. PCT/US2016/21775 dated Jul. 26, 2016.

*Primary Examiner* — Pranav N Patel
(74) *Attorney, Agent, or Firm* — Potomac Law Group, PLLC; Mark Catan

(57) ABSTRACT

Filtering systems, methods, and devices, particularly adapted for apheresis of cellular bodies and more specifically for apheresis of circulating tumor cell bodies (CTCs) employs a cross-flow channel. Systems and methods as well as devices for such a system are described. Embodiments include a cylindrical filter that employs a thin micro-machined porous filter membrane with a regular array of pores and reliably pass blood while trapping CTCs.

19 Claims, 16 Drawing Sheets

(51) Int. Cl.

| | | |
|---|---|---|
| *B01D 61/24* | (2006.01) | |
| *B01D 63/06* | (2006.01) | |
| *B01D 69/02* | (2006.01) | |
| *B01D 71/64* | (2006.01) | |
| *B01D 67/00* | (2006.01) | |
| *B01D 69/10* | (2006.01) | |
| *G01N 33/49* | (2006.01) | |
| *B01D 69/04* | (2006.01) | |

(52) U.S. Cl.
CPC ........ *A61M 1/3403* (2014.02); *A61M 1/3406* (2014.02); *A61M 1/36* (2013.01); *A61M 1/3603* (2014.02); *B01D 63/06* (2013.01); *B01D 67/0032* (2013.01); *B01D 69/02* (2013.01); *B01D 69/04* (2013.01); *B01D 69/10* (2013.01); *B01D 71/64* (2013.01); *G01N 33/491* (2013.01); *A61M 1/3626* (2013.01); *A61M 1/3639* (2013.01); *A61M 1/3672* (2013.01); *A61M 2202/0429* (2013.01); *A61M 2205/3331* (2013.01); *A61M 2205/3334* (2013.01); *B01D 2311/16* (2013.01); *B01D 2311/165* (2013.01); *B01D 2313/025* (2013.01); *B01D 2315/10* (2013.01); *B01D 2325/02* (2013.01); *B01D 2325/021* (2013.01); *B01D 2325/022* (2013.01); *B01D 2325/04* (2013.01)

(58) Field of Classification Search
CPC ........ B01D 2325/021; B01D 2325/022; B01D 2325/028; B01D 2325/04; B01D 2313/025; B01D 2315/10; B01D 63/06; B01D 67/0032; B01D 69/02; B01D 69/04; B01D 69/10; B01D 71/64; A61M 1/34; A61M 1/3403; A61M 1/3406; A61M 1/341; A61M 1/36; A61M 1/3603; A61M 1/3626; A61M 1/3635; A61M 1/3639; A61M 1/3672; A61M 2202/3331; A61M 2205/3331; A61M 2205/3334; A61M 2311/16; A61M 2311/165; G01N 33/491

See application file for complete search history.

(56) References Cited

U.S. PATENT DOCUMENTS

| | | |
|---|---|---|
| 2011/0287948 A1 | 11/2011 | Suresh et al. |
| 2012/0253257 A1 | 10/2012 | Tamari |
| 2013/0197420 A1 | 8/2013 | Fissell et al. |
| 2013/0270165 A1 | 10/2013 | Shevitz |
| 2014/0008210 A1 | 1/2014 | Guia et al. |
| 2014/0061115 A1* | 3/2014 | DiBiasio .............. B01D 63/082 210/321.72 |
| 2014/0299532 A1 | 10/2014 | Becker et al. |
| 2014/0339161 A1 | 11/2014 | Leonard et al. |
| 2015/0041398 A1 | 2/2015 | Rijn et al. |

FOREIGN PATENT DOCUMENTS

| | | | |
|---|---|---|---|
| WO | WO2013052951 | * | 4/2013 |
| WO | 2014072284 A1 | | 5/2014 |

* cited by examiner

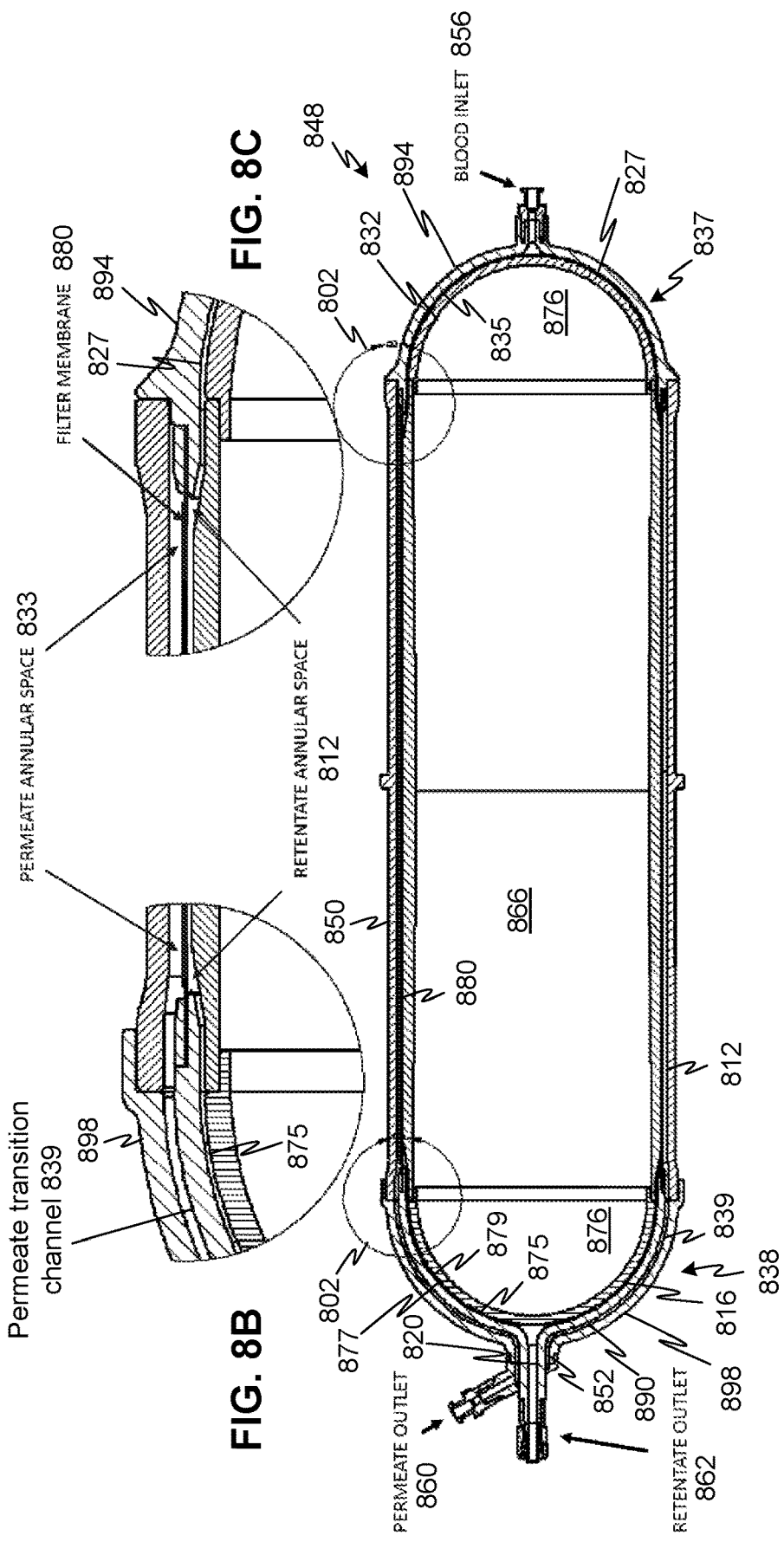

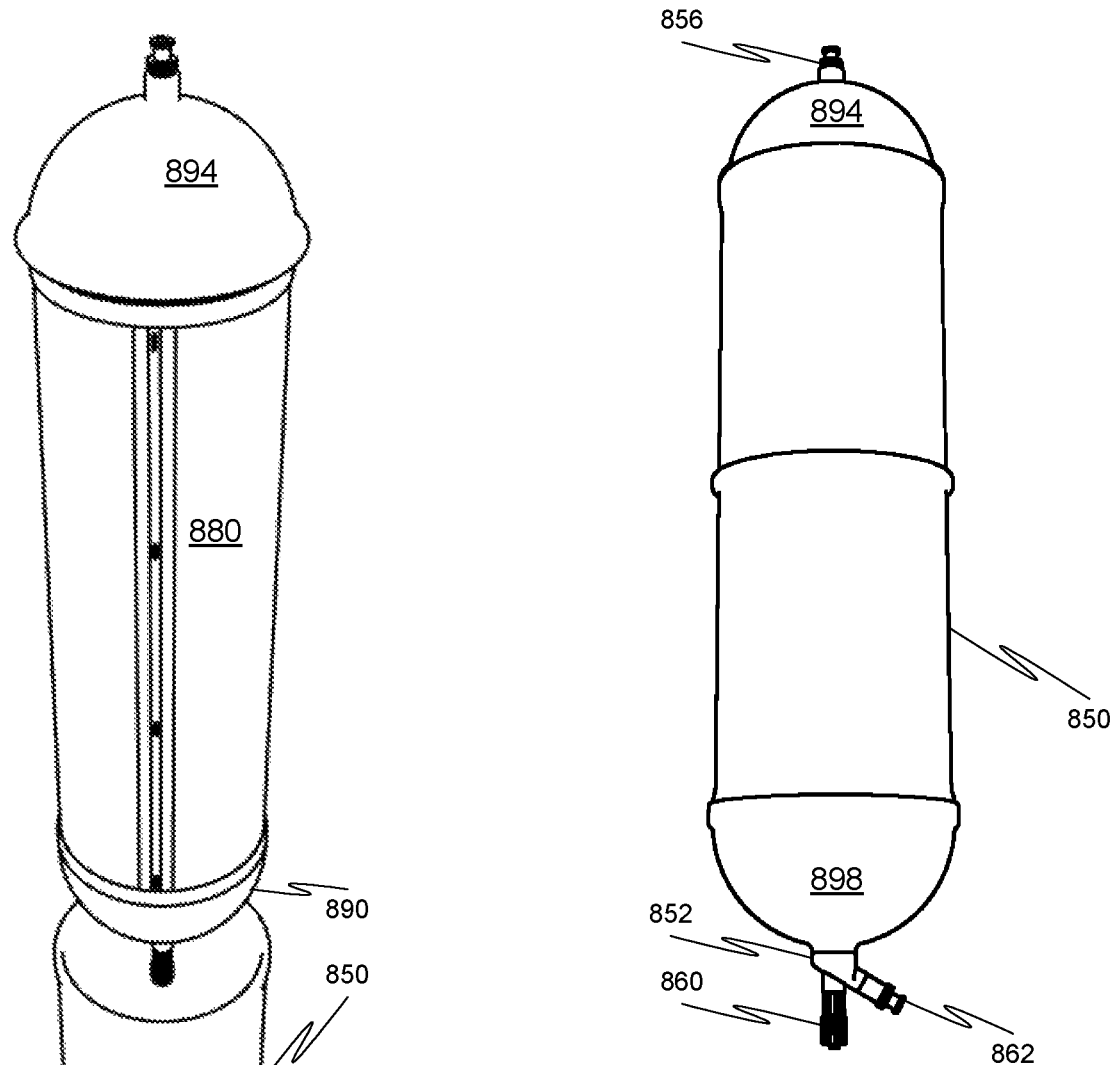
FIG. 9N
FIG. 9P
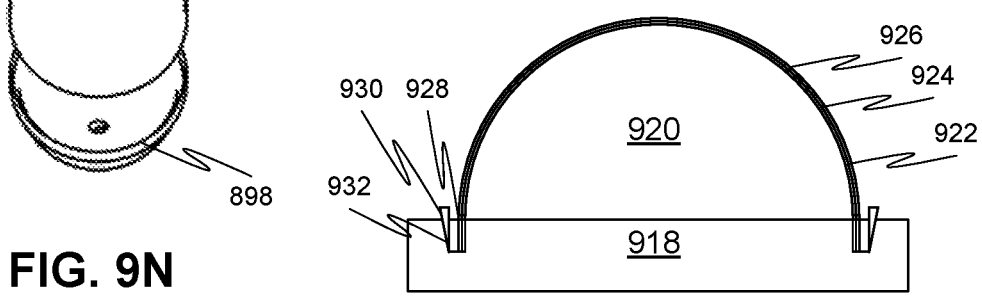
FIG. 11

SYSTEMS, METHODS, AND DEVICES FOR REMOVING CIRCULATING TUMOR CELLS FROM BLOOD

CROSS-REFERENCE TO RELATED APPLICATIONS

This application is a U.S. national stage filing under 35 U.S.C. § 371 of International Application No. PCT/US2016/021775 filed Mar. 10, 2016, which claims the benefit of U.S. Provisional Application No. 62/131,075, filed Mar. 10, 2015, both of which are hereby incorporated by reference in their entireties.

FIELD

The present disclosure relates generally to blood filtration and processing, and, more particularly, to removal of circulating tumor cells (CTCs) from whole blood.

SUMMARY

In one or more embodiments of the disclosed subject matter, a method of removing circulating tumor cells (CTCs) from whole blood comprises flowing the whole blood along a retentate channel of a cross-flow module. A wall of the retentate channel can be formed by a first surface of a filter membrane, which can separate the retentate channel from a permeate channel of the cross-flow module. The filter membrane can be arranged parallel to a direction of fluid flow through the retentate channel. A wall of the permeate channel can be formed by a second surface of the filter membrane opposite to the first surface. The method can further comprise, at the same time as the flowing along the retentate channel, flowing fluid along the permeate channel, which fluid has passed through the filter membrane into the permeate channel and includes at least red blood cells from the whole blood. The method can also comprise controlling a flow rate of the flowing along the retentate channel and/or a flow rate of the flowing along the permeate channel such that a per-pore flow rate of red blood cells through the filter membrane is less than a characteristic red blood cell passage rate for said filter membrane. The filter membrane can have an array of tapered pores extending from one of the first and second surfaces to the other of the first and second surfaces. Each pore can have a first cross-width dimension at said one of the first and second surfaces of the filter membrane greater than a nominal cross-width dimension at said other of the first and second surfaces of the filter membrane. Each pore can be sized to obstruct passage of CTCs therethrough.

In one or more embodiments, a method of removing circulating tumor cells (CTCs) from whole blood comprises, for at least an hour, continuously flowing whole blood along and parallel to a first side of a filter membrane while withdrawing filtrate that has passed through to a second side of the filter membrane opposite the first side such that red blood cells from the whole blood pass through the filter membrane without a rise in transmembrane pressure exceeding 100 torr over the at least an hour. The filter membrane can have an array of pores, each of which tapers with respect to a thickness direction of the filter membrane from one of the first and second sides to the other of the first and second sides. Said one of the first and second sides can have a greater open area than said other of the first and second sides of the filter membrane.

In one or more embodiments, a system for removing circulating tumor cells (CTCs) from whole blood comprises a cross-flow module and a controller. The cross-flow module can have a retentate channel, a permeate channel, and a filter membrane. The filter membrane can separate the retentate channel from the permeate channel and can be arranged parallel to a direction of fluid flow through the retentate channel. The filter membrane can also have an array of tapered pores extending through the filter membrane. Each pore can have a cross-width dimension that narrows from one of the retentate and permeate channels to the other of the retentate and permeate channels. The controller can be configured to control at least a flow rate of whole blood through the retentate channel and/or a flow rate of fluid along the permeate channel responsively to a signal indicative of a rise in transmembrane pressure of the filter membrane.

In one or more embodiments, a cross-flow filter is disclosed which provides a stable cross-section for maintenance of uniform shear rates despite employing a very thin filter membrane. In embodiments, this is achieved in part by forming cylindrical channels or other channels such as helical that translate the force of pressure to tension in the thin membrane without high leverage such that the resistance of the membrane to stretching can maintain the retentate channel depth despite high trans-membrane pressure.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

FIGS. 8A-8D show a crossflow filter device and particular details thereof according to embodiments of the disclosed subject matter.

FIGS. 9A-9H, 9J-9N and 9P show stages of assembly of the filter device of FIGS. 8A-8D according to embodiments of the disclosed subject matter.

FIG. 10 shows a view inside a recess of a component of the filter device of FIGS. 8A-8D according to embodiments of the disclosed subject matter.

FIG. 11 illustrates an alternative structure with features common to those of the filter module of FIGS. 8A-8D and other disclosed embodiments.

DETAILED DESCRIPTION

In embodiments of the disclosed subject matter, a statistically significant quantity of circulating tumor cells (CTCs), for example, on the order of $10^2$ to $10^6$ cells, can be removed from whole blood using a cross-flow filter module as part of a diagnostic or treatment modality. The cross-flow filter module can include a filter membrane that separates an inlet retentate channel from an outlet permeate channel. The filter membrane can have with an array of uniformly-sized (i.e., within 10%) and uniformly-spaced (i.e., with 10%) pores that extend through a thickness of the filter membrane and provide a fluid path between the retentate and permeate channels. The cross-width dimension of each pore (e.g., the diameter for a circular pore or the minimum width for a rectangular pore) is selected to allow desired components of whole blood to pass therethrough (e.g., red blood cells, white blood cells, and/or platelets) while preventing or at least obstructing passage of CTCs. For example, each pore can have the same nominal cross-width dimension (i.e., the minimum dimension at a bottom of the pore) between 4 µm and 8 µm, for example, a nominal diameter of 6 µm, 7 µm, or 8 µm.

The inlet flow of whole blood provided to the inlet retentate channel can be parallel (or substantially parallel) to a major surface of the filter membrane (i.e., perpendicular to a central axis of the pores) so as to sweep the surface of the filter membrane to prevent, or at least minimize, accumulation of particles or cells on the surface or in the pores of the filter membrane. The flow rates in the filter module can be controlled to avoid clogging or fouling of the filter membrane. For example, the flow rate of whole blood in the retentate channel and the flow rate in the permeate channel are independently controlled such that a characteristic red blood cell passage rate through the filter membrane is not exceeded, which rate may be determined experimentally as described further herein. By such control of the flow rates (and resulting shear rates across the filter membrane and estimated average shear rates through the filter membrane), the filter module can be run continuously for several hours (e.g., 1-4 hours) without fouling (i.e., characterized by a transmembrane pressure rise of greater than 10 torr, for example, 100 torr), thereby allowing one or more entireties (i.e., 4-6 L, for example, 5 L) of a patient's blood volume to be processed in a single treatment session. In embodiments, 2-3 times the patient's blood volume may be processed such that a given volume of blood may be processed as much as 2-3 times over.

Figure 1A:
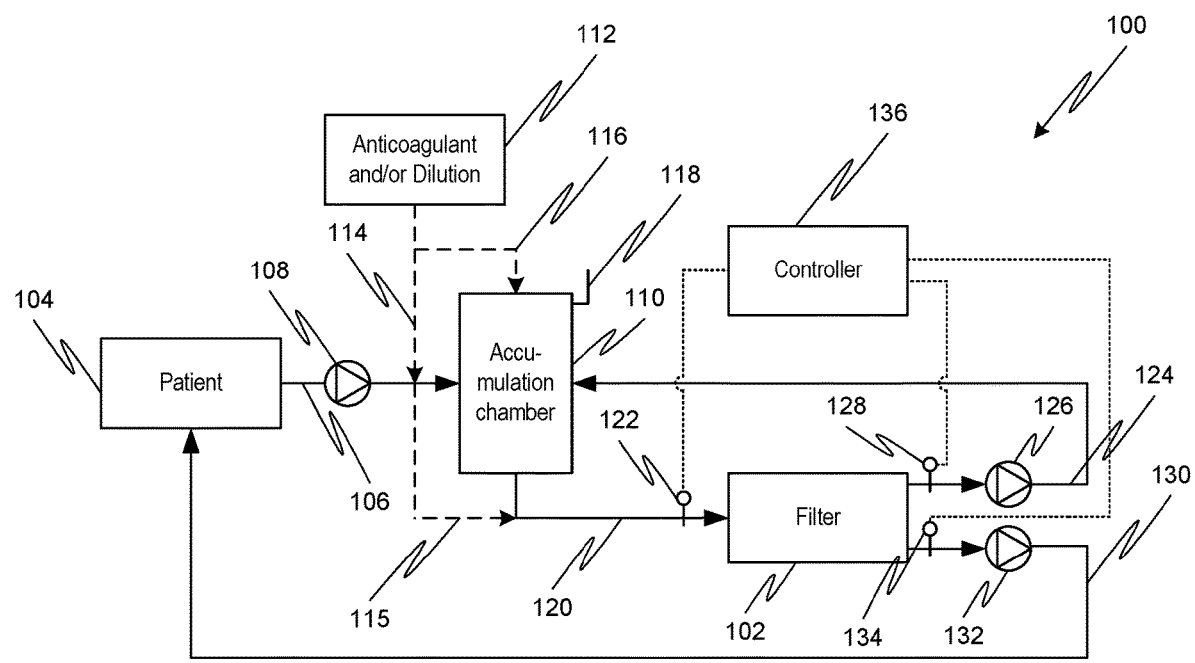
FIG. 1A is a schematic diagram illustrating a setup for removing circulating tumor cells (CTCs) from a patient's blood, according to one or more embodiments of the disclosed subject matter.

FIG. 1A shows an exemplary setup 100 for removing CTCs from whole blood from a patient 104. Cross-flow filter module 102 includes permeate and retentate fluid channels therein. As used herein, permeate channels or lines refer to the channels or lines carrying fluid that has passed through a filter membrane within the cross-flow filter module 102, while retentate channels or lines refer to the channels or lines conveying fluid that has not passed through the filter membrane. Whole blood from the patient 104 can be removed via withdrawal line 106 using a pump 108 (e.g., a positive displacement pump). For example, the whole blood can be withdrawn via central venous catheter, a port, or a peripheral catheter.

The whole blood can be processed by the filter module 102 and returned to the patient via injection line 130. An accumulation chamber 110 can be used to temporarily hold the whole blood from the patient 104 prior to processing by the filter module 102. For example, the accumulation chamber may have a volume of 5-500 ml (e.g., 1 unit of blood) and can have a vent 118 to allow gas within the accumulation chamber to escape. For example, vent 118 can comprise a porous plug or membrane that prevents buildup of pressure in the accumulation chamber 110. Sensors (not shown), such as level sensors and/or gravimetric sensors, can be utilized to monitor the fluid volume in the accumulation chamber 110 to detect any blockages that may arise, for example, in the filter module 102 or in the permeate circuit.

Because the accumulation chamber 110 is provided between the patient 104 and the filter module 102 to hold a volume of blood, the flow rate of whole blood from the patient via withdrawal line 106 can be decoupled from the flow rate of blood in the retentate channel of the filter module 102. Thus, the flow rate of blood from the patient 104 via withdrawal line 106 may be the same as or different from the flow rate of processed blood infused into the patient 104 via infusion line 130 despite a flow rate in the retentate channel that may be significantly different from both flow rates. For example, the flow rate of whole blood from the patient can be in the range of 5-80 ml/min, inclusive, while a flow rate in the infusion line 130 can be in the range of 5-80 ml/min and the flow rate in the retentate channel can be adjusted to maintain a desired shear rate for the particular filter module. In embodiments, the flow rates are 45 ml/min. The volume processed may scale with the filter size. Bubble sensors (not shown) can be placed in the infusion line 130 to detect air bubbles in the return blood flow prior to infusion into the patient.

The whole blood can be diluted and/or have a regional anticoagulant added thereto prior to processing by the filter module 102. For example, anticoagulant can be added to the whole blood before it is added to accumulation chamber 110 via line 114 or while it is in the accumulation chamber 110 via line 116. Alternatively or additionally, anticoagulant can be added to the whole blood after leaving the accumulation chamber 110 via line 115.

Whole blood from the accumulation chamber 110 can be directed along input line 120 to the retentate channel of filter module 102, where it flows along the retentate channel in a direction from an inlet end thereof to an outlet end thereof substantially parallel to a major surface of the filter membrane. The flow at the outlet end of the retentate channel is directed via a recirculating channel 124 back to the accumulation chamber 110, where it is combined with whole blood therein for reprocessing by the filter module 102. A recirculating pump 126 (e.g., a positive displacement pump) controls the flow in the retentate channel and through the recirculating channel 124. Similarly, a permeate pump 132 (e.g., a positive displacement pump) controls the flow in the permeate channel and through the infusion channel 130.

By appropriate control of pumps 126, 132, for example by controller 136, the flow through the filter membrane of the filter module 102 can be regulated. In particular, the recirculating pump 126 can pull whole blood from the accumulation chamber 110 into the retentate channel and across the major surface of the filter membrane in the filter module 102 such that a shear rate is maintained above a minimum value at each point along the major surface to provide sufficient sweeping of the major surface. Such sweeping may be effective to move CTCs that are too large and stiff to pass through the pores of the filter membrane or other cells that have not passed through the pores to the outlet end of the retentate channel for recirculation. Pump flow rates can be adjusted to operate in ranges that prevent, or at least reduce the risk of, hemolysis of red blood cells. For example, the shear rate may be between 500 s$^{-1}$ and 1000 s$^{-1}$.

Transmembrane pressures can be monitored for safety and to prevent hemolysis caused by an occluded filter. A first pressure sensor 122 can be disposed upstream of the inlet end of the retentate channel in the filter module 102. A second pressure sensor 128 can be disposed downstream of the outlet end of the retentate channel in the filter module 102. A third pressure sensor 134 can be disposed downstream of the outlet end of the permeate channel in the filter module 102. The controller 136 can receive signals from the first through third pressure sensors and can regulate flow rates (e.g., by controlling pumps 126, 132) responsively thereto. For example, the controller 136 can calculate an average transmembrane pressure (TMP$_{avg}$) as:

$$TMP_{avg} = \frac{(P_1 + P_2)/2}{\overline{P_3}}$$

where $P_1$ is the pressure measured by the first pressure sensor 122, $P_2$ is the pressure measured by the second pressure sensor 128, and $\overline{P_3}$ is the average pressure measured by the third pressure sensor 134. The controller may respond to increases in transmembrane pressure, for example, by increasing the retentate channel flow rate to improve sweeping and/or adjusting permeate channel flow rate, while also taking into account the characteristic red blood cell passage rate for the filter membrane.

Each filter pore size has a characteristic red blood cell passage rate that, if exceeded, causes red cells to back up and foul the surface of the filter over time. By not allowing flows to exceed this characteristic rate, the possibility of occlusion of the filter can be minimized or at least reduced. In order to determine the characteristic red blood cell passage rate for a particular filter membrane, a solution of washed pooled red blood cells is diluted to a known hematocrit. Using this hematocrit and assuming that normal human blood averages 5.0×10$^9$ red blood cells/ml, total permeate flow rates are calculated using different red blood cell passage values. Tests are run by using a single peristaltic pump to pass the diluted solution through the filter membrane at the predetermined total permeate flow rates. Pressure transducers located at the inlet and outlet of the cross-flow filter module can be used to monitor the trans-membrane pressure throughout the duration of the test. The pressure data collected throughout the test can then be used to determine the red blood passage value that would allow the full volume of solution to pass through the filter without a significant increase (e.g., greater than 10 torr increase) in the trans-membrane pressure.

For example, the characteristic red blood cell passage rate may correspond to an estimated or average shear rate through the pores that is less than 350 s$^{-1}$, e.g., approximately 160 s$^{-1}$. For round pores, estimated or average shear rate ($\dot{\gamma}$) can be given by:

$$\dot{\gamma} = \frac{4Q}{\pi r^3}$$

where $\dot{\gamma}$=Shear rate (s$^{-1}$); Q=average volumetric flow rate per pore (cm$^3$/s); and r=radius of nominal opening of pore (cm). Note that Q is given by:

$$Q = \frac{Q_{total}}{n}$$

where $Q_{total}$ is the total flow rate through the filter (e.g., the permeate flow rate) and n is the number of pores for the filter. Similarly, for rectangular pores, estimated or average shear rate ($\dot{\gamma}$) can be given by:

$$\dot{\gamma} = \frac{6Q}{ab^2}$$

where $\dot{\gamma}$=Shear rate (s$^{-1}$); Q=average volumetric flow rate per pore (cm$^3$/s); a=width along long axis at nominal opening of pore (cm); and b=width along short axis at nominal opening of pore (cm).

By maintaining flow through the filter membrane less than the characteristic red blood cell passage rate, fouling of the filter membrane can be avoided. As used herein, fouling of the filter membrane refers to occlusion of the pores of the filter membrane by cells or other detritus that results in a transmembrane pressure rise of over 100 torr. In embodiments of the disclosed subject matter, operation of the filter membrane is controlled to keep any rise in the transmembrane pressure from a start to an end of the processing to less than 10-30 torr. Results of determined characteristic red blood cell passage rates for various filter configurations are shown below in Table 1.

In some embodiments, the filtering devices and methods disclosed herein can be used to filter about 70-100%, or about 90-99% (e.g., at least about 70, 75, 80, 85, 90, 95, 99, 99.5, or 99.9%, or any value in between) of the blood or other bodily fluid from the patient 104 via peripheral or central venous vascular access after the first passage through the cross-flow filter 102. The filtered fluid enters the permeate channel and is returned to the patient 104. The remaining blood or other bodily fluid is retained in the recirculation channel 124. For example, this can mean, in terms of blood flow rates, that if via the vascular access 100 ml/min is drawn from the patient 104, then the flow rate of the recirculating retentate can be set at 1-10 ml/min in steady state with aid of a recirculation pump 126 in order to allow for sufficient fluid to pass through the filter 102 to filter at least about 70% of the fluid on the first pass. The flow rate of the permeate fluid, as it is returned to the patient 104 in steady state, can be set with aid of the permeate pump 132 to the same rate as the vascular access flow rate drawn from the patient (e.g., 100 ml/min).

TABLE 1

Characteristic Red Blood Cell Passage Rate for Various Filter Sizes/Orientations.

| Nominal Pore Size (μm) | Geometry | Dimple Orientation | Passage Rate (RBC/pore/sec) |
| --- | --- | --- | --- |
| 6 | Round | Down | 75 |
| 7 | Round | Down | 75 |
| 8 | Round | Down | 2500 |
| 4 × 12 | Rectangle | Down | 25 |
| 6 × 12 | Rectangle | Down | 400 |
| 8 × 12 | Rectangle | Down | 600 |
| 4 × 22 | Rectangle | Down | 50 |
| 6 × 22 | Rectangle | Down | 800 |
| 8 × 22 | Rectangle | Down | 5000 |
| 6 | Round | Up | 150 |
| 7 | Round | Up | 150 |
| 8 | Round | Up | 5000 |
| 4 × 12 | Rectangle | Up | 50 |
| 6 × 12 | Rectangle | Up | 800 |
| 4 × 22 | Rectangle | Up | 100 |
| 6 × 22 | Rectangle | Up | 1600 |
| 8 × 22 | Rectangle | Up | 10,000 |

CTCs that do not pass through the filter membrane of the filter module 102 flow to the outlet end of the retentate channel and then to the accumulation chamber 110 via the recirculating line 124. Repetitive recirculation of the retentate through the filter module 102 can concentrate the retentate with increasing quantities of CTCs. As a result, the CTCs filtered by the filter module 102 from the whole blood will concentrate in the accumulation chamber 110. The CTCs in the accumulation chamber 110 can be collected at the end of treatment for disposal or further analysis.

Figure 1B:
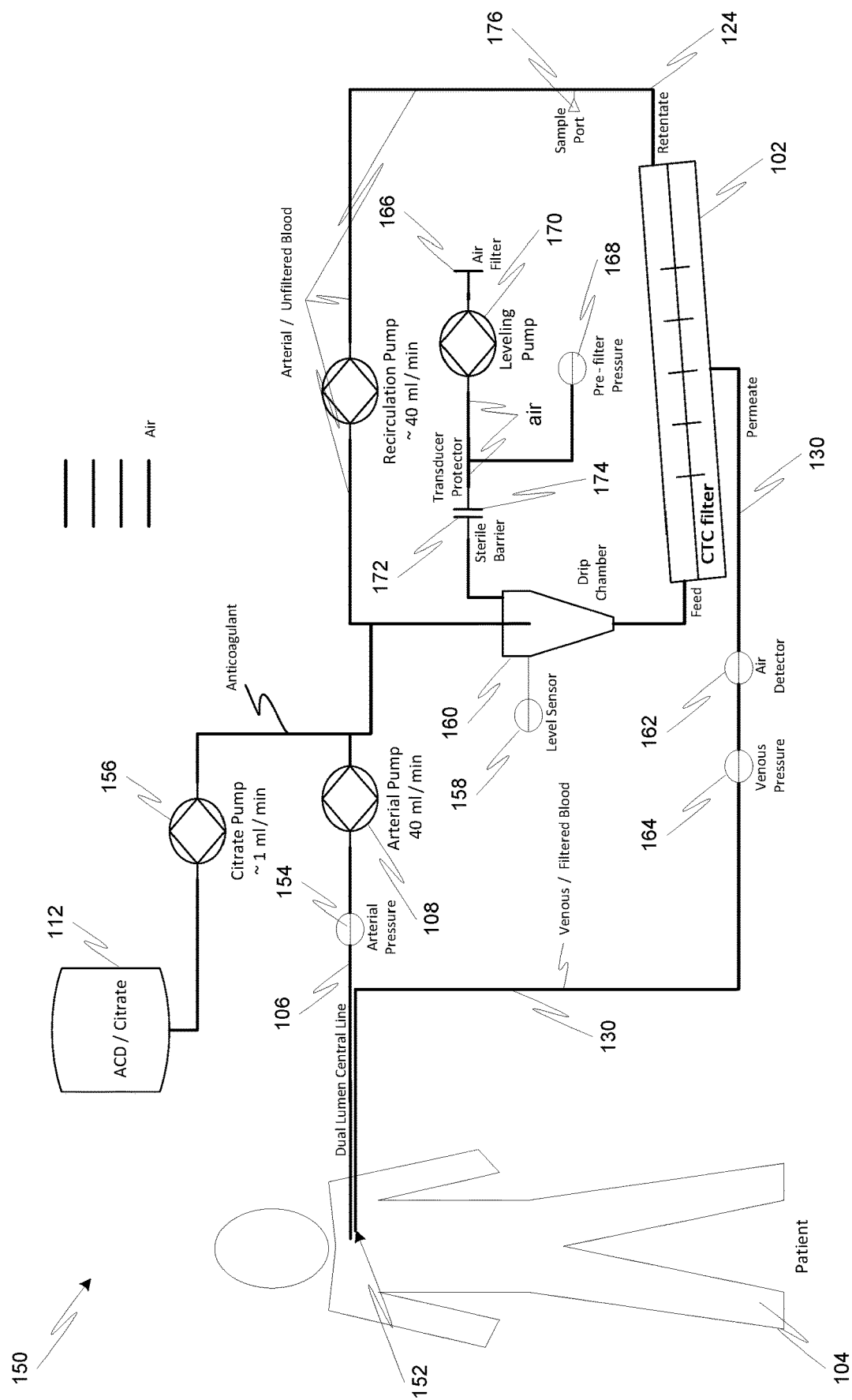
FIG. 1B is a schematic diagram illustrating an alternative setup for removing CTCs from a patient's blood, according to one or more embodiments of the disclosed subject matter.

Other configurations for the fluid setup to/from the patient 104 and/or the filter module 102 are also possible according to one or more contemplated embodiments. For example, a setup 150 without a permeate pump is shown in FIG. 1B. A dual lumen central line 152 can be used to withdraw blood from the patient 104 and to infuse fluid back into the patient 104 via an arterial line 106 and a venous/permeate line 130, respectively. The arterial line 106 can be provided with an arterial pressure sensor 154, which measures the pressure in the arterial blood line 106. A low arterial pressure reading can indicate an obstructed arterial blood line 106.

Blood flow from the patient 104 can be controlled by an arterial pump 108, which may be a peristaltic noncontact pump. The flow in the venous blood line 130 is equal to the permeate flow through the filter module 102. Since the system is closed, conservation of mass ensures that the permeate flow rate is equal to the sum of the arterial pump 108 flow, the citrate pump 156 flow, and the leveling pump 170 flow. Thus, the arterial pump 108, in combination with the other pumps, can regulate the flow in the arterial 106 and venous 130 blood lines. For example, the arterial pump 108 flow rate can be 40 ml/min.

The blood from the patient 104 along with anticoagulant (e.g., Anticoagulant Citrate Dextrose (ACD)) and/or dilution fluid via citrate pump 156 can be fed to a chamber 160, which may be a drip chamber. The citrate pump 156 can be a peristaltic noncontact pump. The citrate pump 156 can deliver ACD to the blood circuit at a prescribed rate, for example, around 2.5% of the arterial pump 108 speed, so as to prevent or at least reduce coagulation.

The drip chamber 160 can be part of a disposable or consumable component of the system, which can also include one or more of the blood lines (i.e., arterial line 106, venous line 130, and recirculation line 124) and the filter module 102. The drip chamber 160 can separate air from the blood prior to it entering the filter module 102. The level in the drip chamber 160 can be controlled by a leveling pump 170, which may be a reversible air pump. For example, a level sensor 158 can detect the level of the blood/air interface in the drip chamber 160 and provide a signal indicative of the measured level to a controller (not shown). If the level is low (e.g., with respect to a predetermined first or minimum level), the leveling pump 170 can be instructed to remove air. If the level is high (e.g., with respect to a predetermined second or maximum level), the leveling pump 170 can be instructed to add air. Air input to the leveling pump 170 can filtered by air filter 166 to eliminate, or at least reduce, introduction of dust and debris to the pump and tubing.

The control line from the leveling pump 170 to the drip chamber 160 can be supplied with a sterile barrier 172, which may be a hydrophobic filter. The sterile barrier 172 can protect the blood tubing set from contamination and can also ensure that blood does not escape the disposable component into the reusable components of the system via the level control air lines. The air control line can also include a transducer protector 174, which can be a second hydrophobic filter and can serve to further ensure that blood that blood does not escape the disposable component. The air control line can further include a pre-filter pressure transducer 168, which measures the air pressure in the drip chamber 160. The air pressure in the drip chamber 160 should be the same (or substantially the same, e.g., within 10%) as the pressure in the feed line of the filter module 102. The difference between the pressure measured by the pre-filter transducer 168 and the pressure measured by the venous transducer 164 is the transmembrane pressure drop across the filter membrane of the module 102 and can be used to indicate a clogged filter membrane.

Blood and ACD from the drip chamber 160 are provided to the filter module 102 via a feed line such that the fluid flows through a retentate channel in the filter module 102 across one side of a filter membrane in the module 102. The filter module 102 may be angled or tilted (with respect to horizontal) at one end to assist in the removal of air from the system during priming. Fluid at the opposite end of the retentate channel exits the filter module into a recirculating channel 124, where a recirculation pump 126 directs the fluid back to drip chamber 160 for further processing. The recirculation pump 126 can be a peristaltic noncontact pump. For example, the flow rate of the recirculation pump 126 can be 40 ml/min. The recirculating channel 124 can also include a sample port 176, which allows for the drawing of samples of the retentate.

Fluid passing through the filter membrane of the filter module 102 passes into the venous/permeate line 130 for return to the patient 104 via dual lumen central line 152. The venous line 130 can include an air detector 162 to monitor for the presence of air before the fluid is returned to the patient. In the event of detected air in the venous line 130, the arterial pump 108 can be stopped, or other remedial measures may be taken, to stop the flow in the venous line 130. The venous line 130 can also include a venous pressure sensor 164 that measures the pressure in the venous blood line 130. As noted above, the difference between the pressure measured by the pre-filter sensor 168 and the pressure measured by the venous sensor 164 is the transmembrane pressure drop across the filter membrane of the filter module 102 and can be used to indicate a clogged filter. In addition, a high pressure reading by the venous sensor 164 can indicate an obstructed venous blood line.

Figure 2A:
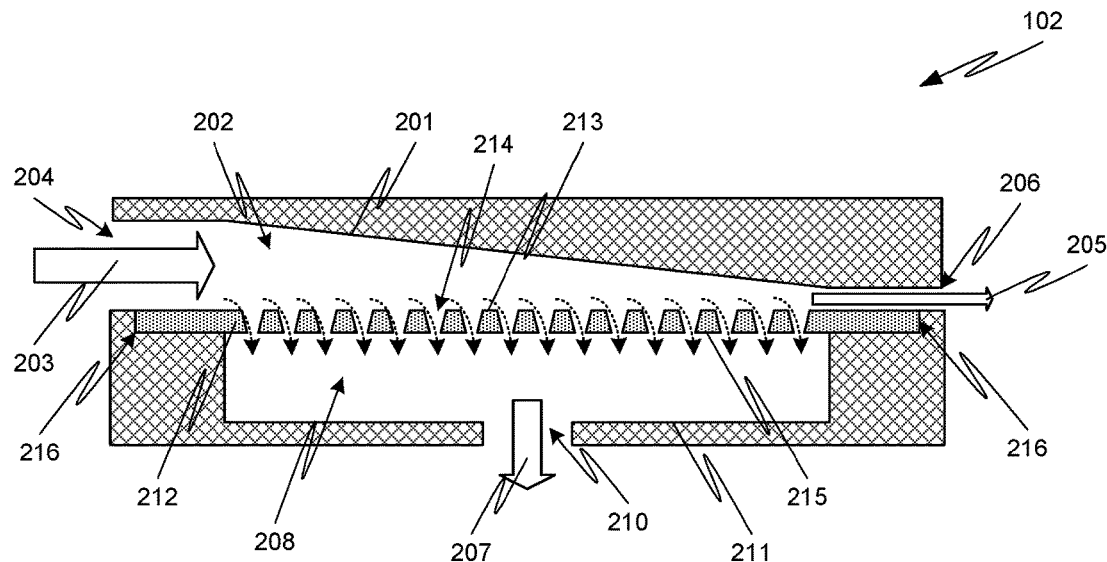
FIG. 2A is a cross-sectional view showing arrangement of channels and a filter membrane in a cross-flow module, according to one or more embodiments of the disclosed subject matter.

Referring now to FIG. 2A, details of the filter module 102 will be discussed. As discussed above, the filter module 102 includes a retentate channel 202 separated from a permeate channel 208 by a filter membrane 212. The retentate channel 202 may be formed between a first major surface 213 of the filter membrane 212 and a top wall 201 of the filter module 102. The permeate channel 208 may be formed between a second major surface 215 of the filter membrane 212 and a bottom wall 211 of the filter module. Attachment structures 216 may be used to secure the filter membrane 212 with respect to other portions of the filter module 102 forming the retentate and permeate channels. An array of pores 214 can extend through a thickness of the filter membrane 212, from the first major surface 213 to the second major surface 215, so as to fluidically connect the retentate channel 202 to the permeate channel 208.

Whole blood 203 is provided to an inlet end 204 of the retentate channel 202 and flows substantially parallel to major surface 213 to an outlet end 206, where the exiting flow 205 is provided to the recirculation line 124 for subsequent reprocessing. Cells and fluid passing through the filter membrane 212 into the permeate channel 208 flow to an outlet portion 210 thereof (for example, a bottom of the filter module 102 facing the filter membrane 212, as illustrated in FIG. 2A, or at an end of the permeate channel 208 in a direction parallel to the filter membrane 212 similar to the arrangement of the outlet 206 of the retentate channel 202), where the exiting flow 207 is provided to the infusion line 130 for infusion into the patient 104.

Figure 2B:
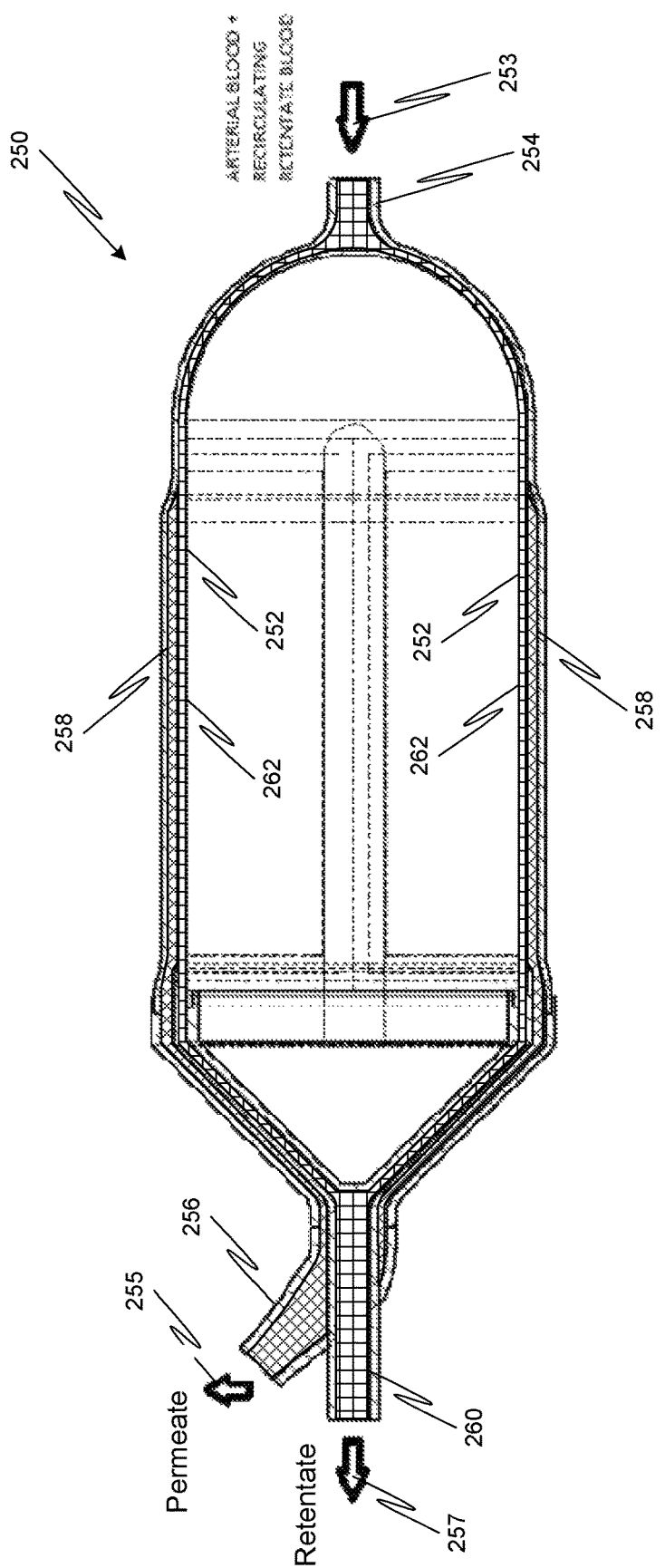
FIG. 2B is a cross-sectional view of a cylindrical cross-flow module, according to one or more embodiments of the disclosed subject matter.

In some embodiments, the retentate channel 202 has a tapered cross-section (e.g., by inclination of top wall 201) in order to maintain a constant shear rate as the retentate fluid flows through the filter module 102. Because a large fraction of the whole blood will permeate through the filter membrane 212, it may be desirable to lower the channel height of the retentate channel 202 near the outlet end 206 with respect to the inlet end 204, as shown in FIG. 2. For example the retentate channel height (i.e., between top wall 201 and filter surface 213) might linearly taper from 100 µm to 50 µm along its length. Normal fluid mechanics can be used to calculate the shear rate along the retentate flow channel and to implement an adequate tapering of the retentate channel from inlet end 204 to outlet end 206 or design other dimensional aspects (e.g., width, length and fixed channel height). The permeate channel 208 may have a fixed channel height (i.e., between bottom wall 211 and filter surface 215), as illustrated in FIG. 2. Alternatively, the permeate channel may have a tapered cross-section along its length in order to compensate for and/or to maintain a constant trans-membrane pressure.

CTCs tend to be at least 8 µm and larger, while red blood cells are typically 2-3 µm thick and 8 µm in diameter. Thus, the pores in the filter membrane may have a nominal dimension smaller than the CTC size to prevent passage of the CTCs therethrough. Since red blood cells are generally more deformable than the CTCs, they may pass more readily through pores that otherwise prevent CTC passage. However, Applicants have found that when the pores size is reduced below 4 µm that the red blood cell passage rate drops precipitously. Accordingly, the filter membrane can be made with, for example, round pores with a nominal diameter, $d_2$ (see FIGS. 3A and 3C), between about 4 µm and 8 µm (e.g., about 4 µm, 5 µm, 6 µm, 7 µm, or 8 µm, or any size in between), or slit-shaped pores with a nominal width between 4 µm and 8 µm (e.g., about 4 µm, 5 µm, 6 µm, 7 µm, or 8 µm, or any size in between) and a length between 4 µm and 40 µm. The specific shape and dimensions of the pores can be chosen for substantially complete permeation of at least red blood cells while retaining a significant fraction of CTCs.

The filter membrane 212 can be fabricated from a polymer film (such as, but not limited to, polyimide, polyethylene terephthalate, and polycarbonate). For example, the pores can be formed in the polymer film by laser ablation using a mask projection laser machining process. This fabrication process yields pores that are tapered from one side to the other. The side of the filter membrane at which the laser energy first penetrates is larger than the side of the filter membrane from which the laser energy exits. The size of the exit hole is the nominal size of the pore. Placing the filter such that the nominal pore dimensions are at the retentate side can result in higher capture efficiency of CTCs at approximately 50% lower red blood cell passage rate, while placing the filter such that the nominal pore dimension is at the permeate side can result in roughly a 50% higher passage rate for red blood cells at a slightly reduced capture efficiency of CTCs. Tapering the entrance to the pore thus allows for more efficient red blood cell passage at the expense of passing some CTCs into the permeate stream.

Figure 3A:
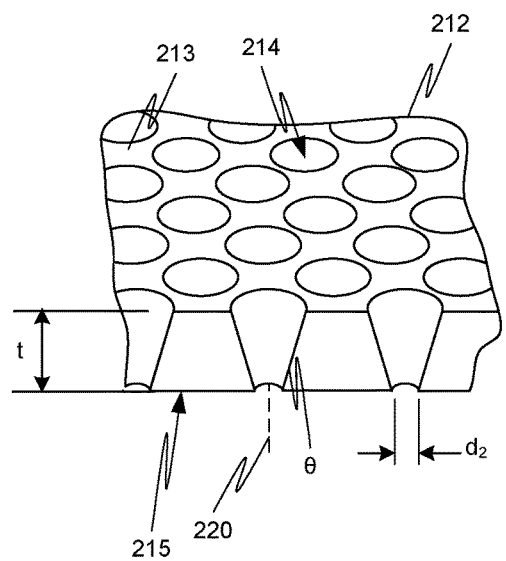
FIG. 3A is an illustration of a uniform array of tapered pores in a filter membrane for use in a cross-flow module, according to one or more embodiments of the disclosed subject matter.

As shown in FIGS. 2A and 3A, the filter membrane 212 can be oriented such that the nominal diameter d2 (or minimal cross-width dimension) of each pore 214 is at the permeate side while the larger entrance diameter d1 (or maximum cross-width dimension) of each pore 214 is at the retentate side. The taper may extend across the entire thickness of the filter membrane 212. For example, the filter membrane can have an overall thickness, t, in a range of 1-50 µm. Alternatively, the taper may extend partially across the thickness, such that a portion of the pore has a constant nominal cross-sectional width, for example, over less than 1 µm at the nominal diameter end, or over between 1 µm and 10 µm at the nominal diameter end. The taper angle, $\theta$, may be determined with respect to the central axis 220 of the pore 214 and may be 11°±3°, for example, 11.31°. In laser machining embodiments, the taper angles may be higher. For example up to 25°. In examples which have been fabricated, the taper angle in is in the range of 18-22°.

In experiments with laser machining using various polymers it was determined that a spacing that is too low can make manufacturing more difficult because of the properties of laser machining. It is believed that adverse reflection due to shaping of the pores can cause undesired artifact in the finished membrane filter. This effect may occur at pore spacing of less than 20 μm. Since a larger spacing requires a larger filter membrane for a given number of pores, it is desirable to minimize the spacing until just short of the threshold where manufacturing quality degrades. In embodiments, the spacing is in the range of 20-30 μm and in further embodiments, the spacing is 23-27 μm. Examples have recently been manufactured with a spacing of 25 μm.

The pore spacing and size can be adjusted so that an open area at one surface is in a range from 40% to at least 90% and an open area at an opposite surface is in a range from 7% to 15%. However, the open area, pore spacing, and size may be a function of desired flow rates, taper angle, and material dimensions (e.g., thickness of the filter membrane), and thus values other than those specified above are also possible according to one or more contemplated embodiments.

The filter module can be configured in any shape as long as the permeate channel is separated from the retentate channel by the filter membrane. For example, the filter module may have a substantially planar arrangement as illustrated by the cross-sectional view of FIG. 2A. In another example, the filter module can have a cylindrical arrangement, as illustrated by the cross-sectional view of filter module 250 in FIG. 2B. In such a configuration, a cylindrical permeate channel 252 is arranged radially inward from a cylindrical retentate channel 258 and separated therefrom by cylindrical filter membrane 262. An inlet flow 253 of blood is provided to the filter module 250 via inlet 254 of the retentate channel 258. An outlet flow 255 from the outlet 256 of the retentate channel 256 can be directed back to the inlet 254 via a recirculating line while an outlet flow 257 from the outlet 260 can be directed back to the patient and/or for disposal or further analysis. Although the permeate channel 252 is illustrated as radially inward from the retentate channel 258, is also possible for the orientation to be reversed, i.e., with the permeate channel radially outward of the retentate channel. Other configurations for the filter module as well as the filter membrane and the retentate and permeate channels are also possible according to one or more contemplated embodiments.

Figure 3B:
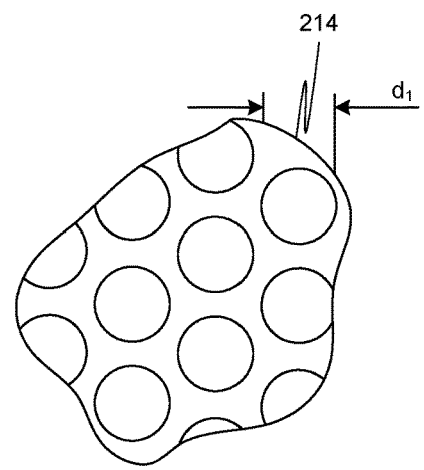
FIG. 3B is an image of a first surface of the filter membrane illustrating a wide end of tapered round pores, according to one or more embodiments of the disclosed subject matter.
Figure 3C:
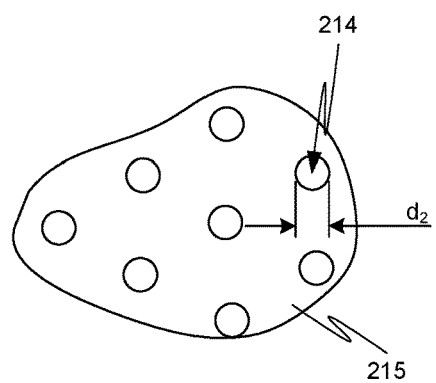
FIG. 3C is an image of a second surface of the filter membrane illustrating a narrow end of tapered round pores, according to one or more embodiments of the disclosed subject matter.
Figure 4A:
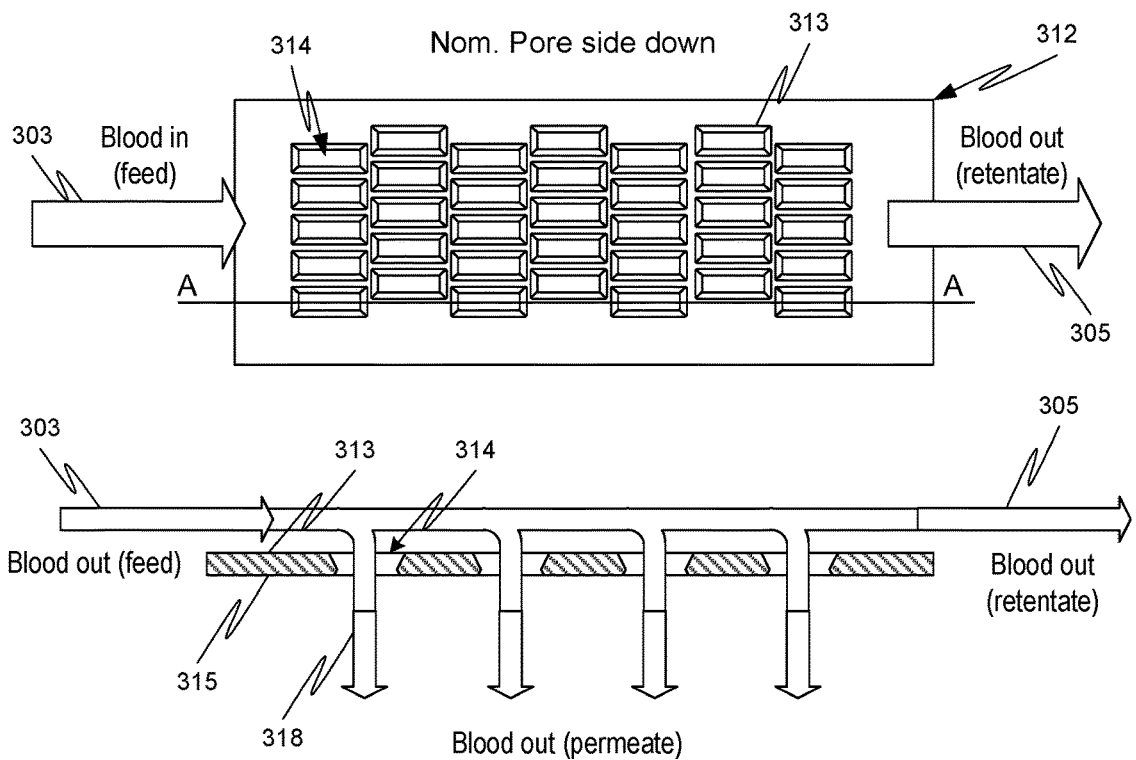
FIG. 4A shows a top view (from the retentate channel) and a cross-sectional view (along line A-A) of a filter membrane with tapered rectangular pores extending parallel to the blood flow and in a nominal pore side down configuration, according to one or more embodiments of the disclosed subject matter.
Figure 4B:
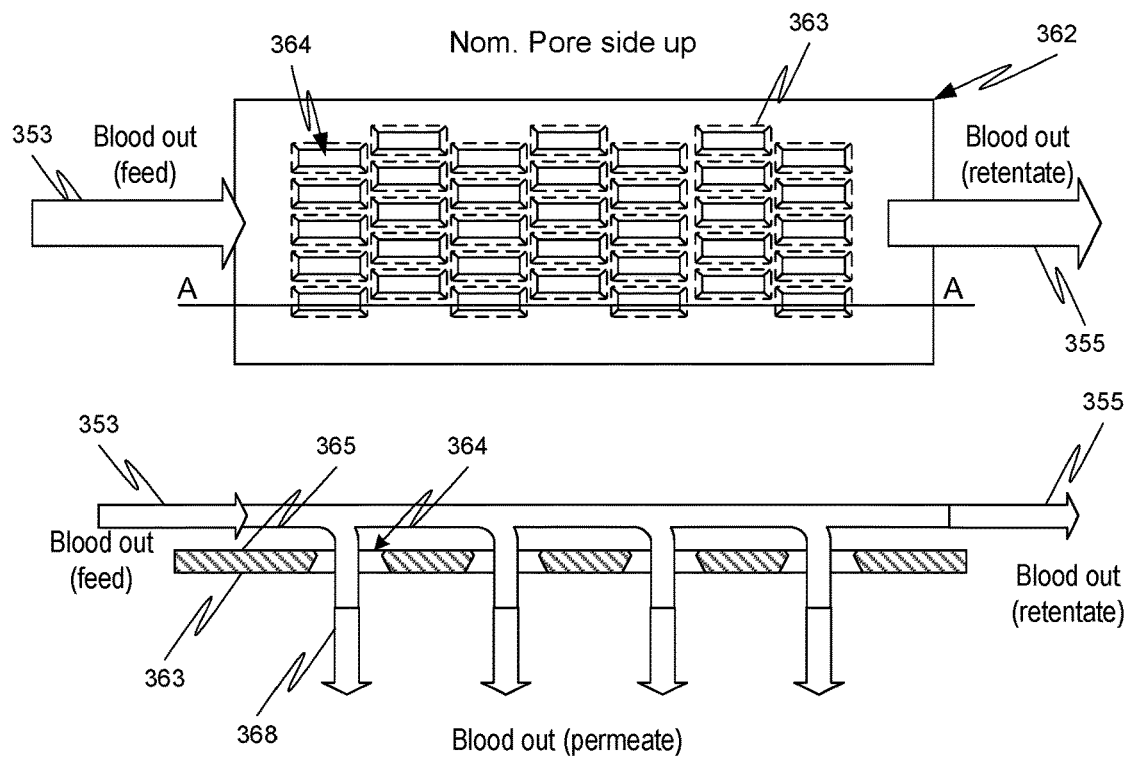
FIG. 4B shows a top view (from the retentate channel) and a cross-sectional view (along line B-B) of a filter membrane with tapered rectangular pores extending parallel to the blood flow in a nominal pore side up configuration, according to one or more embodiments of the disclosed subject matter.
Figure 4C:
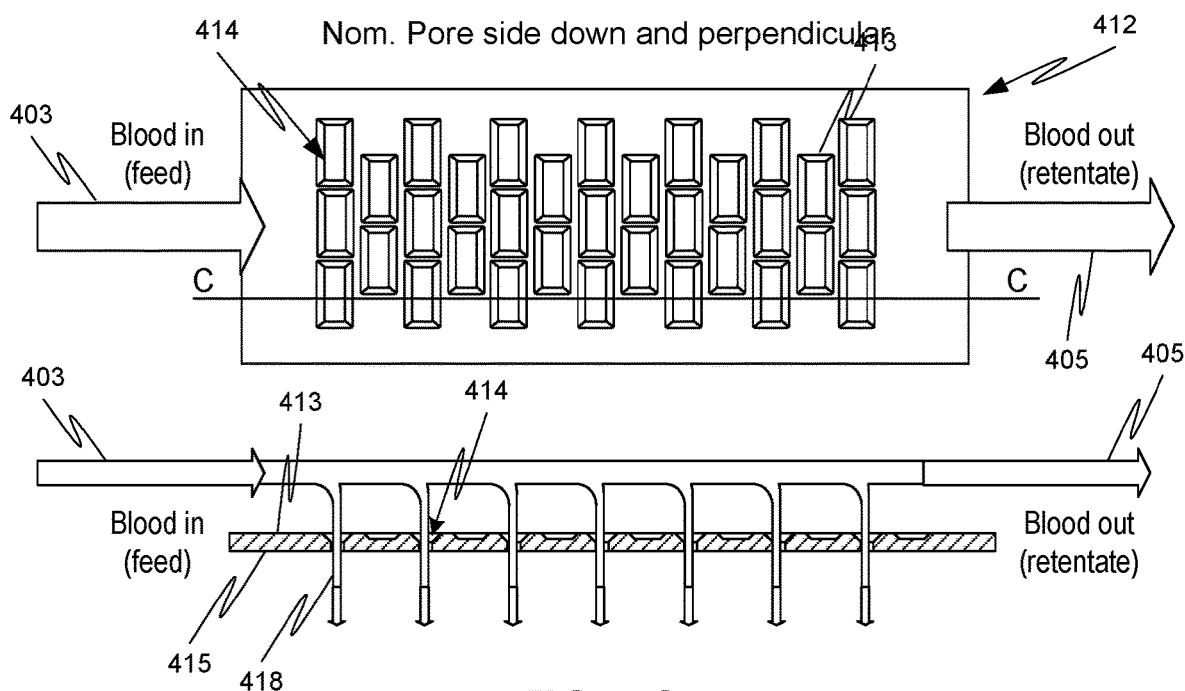
FIG. 4C shows a top view (from the retentate channel) and a cross-sectional view (along line C-C) of a filter membrane with tapered rectangular pores extending perpendicular to the blood flow and in a nominal pore side down configuration, according to one or more embodiments of the disclosed subject matter.
Figure 4D:
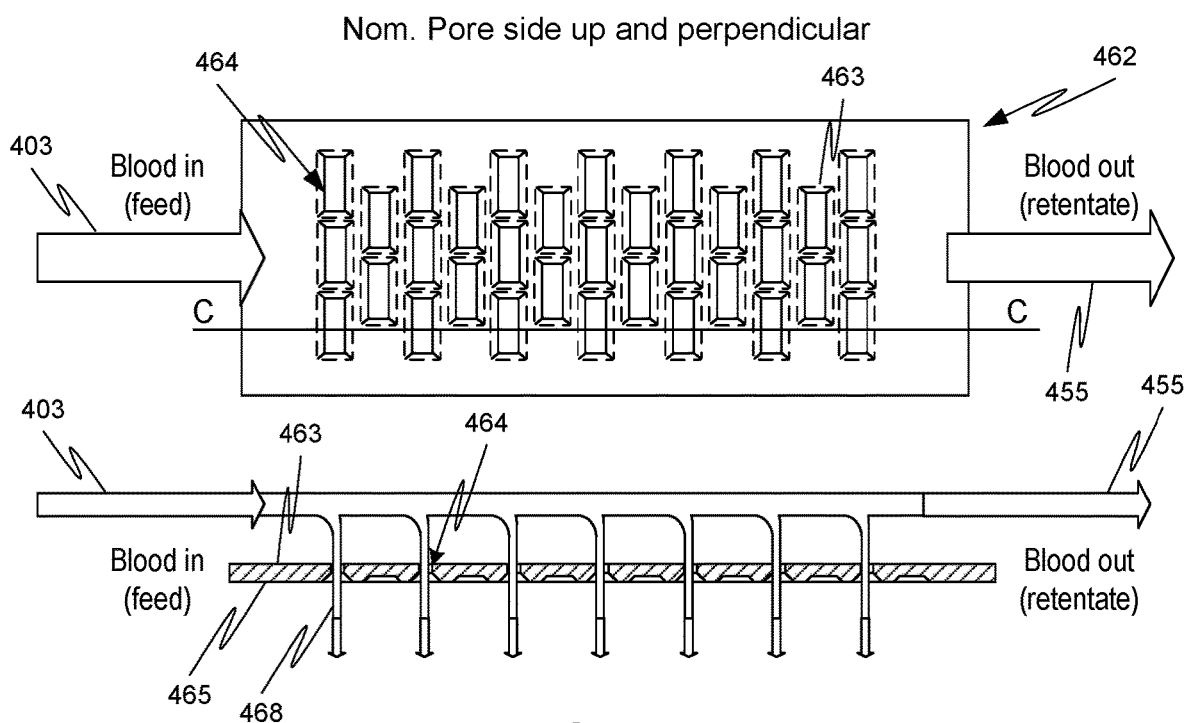
FIG. 4D shows a top view (from the retentate channel) and a cross-sectional view (along line D-D) of a filter membrane with tapered rectangular pores extending perpendicular to the blood flow in a nominal pore side up configuration, according to one or more embodiments of the disclosed subject matter.

In addition, other geometries are also possible for the pore cross-section than the circular cross-section illustrated in FIGS. 3A-3C. For example, each pore may have a rectangular cross-section, as illustrated in FIGS. 4A-4C. In particular, filters with rectangular pores 314/364 may be fabricated such that the long axis of each pore is in the direction of the cross flow of retentate (as per inlet flow 303/353 and outlet flow 305/355), as illustrated in FIGS. 4A-4B. Alternatively, filters with rectangular pores 414/464 may be fabricated such that the short axis of each pore is in the direction of cross flow of retentate (as per inlet flow 403/453 and outlet flow 405/455), as illustrated in FIGS. 4C-4D. The capture efficiency and characteristic red blood cell passage rate at a particular set volumetric flow rate setting may be affected by this orientation.

In particular, FIG. 4A illustrates the configuration with the nominal dimension adjacent the permeate channel, such that fluid 318 passes through each pore 314 from a higher open area surface 313 to a lower open area surface 315, while FIG. 4B illustrates the configuration with the nominal diameter adjacent the retentate channel, such that fluid 368 passes through each pore 364 from a lower open area surface 365 to a higher open area surface 363. FIG. 4C illustrates the configuration with the nominal dimension adjacent the permeate channel, such that fluid 418 passes through each pore 414 from a higher open area surface 413 to a lower open area surface 415, while FIG. 4D illustrates the configuration with the nominal diameter adjacent the retentate channel, such that fluid 468 passes through each pore 464 from a lower open area surface 465 to a higher open area surface 463.

Cross-width shapes other than circular and rectangular are also possible according to one or more contemplated embodiments. For example, the pores may have an elliptical, square, polygonal, oval, or any other geometric shape.

EXAMPLES

Figure 5:
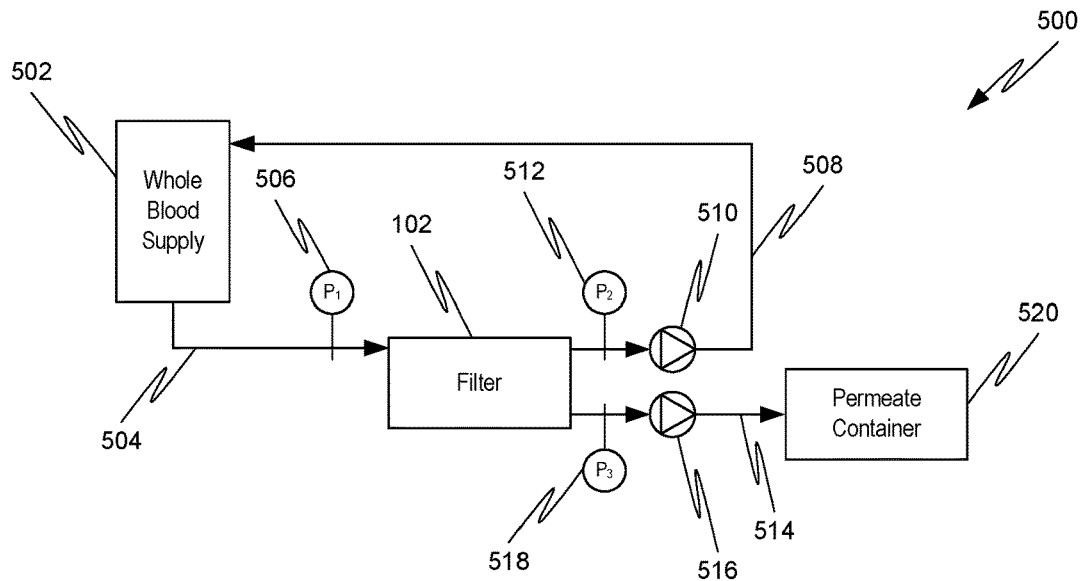
FIG. 5 is a schematic diagram illustrating a testing setup for a cross-flow module with filter membrane for removing circulating tumor cells (CTCs) from whole blood, according to one or more embodiments of the disclosed subject matter.

FIG. 5 illustrates a setup 500 used to perform testing of various filter membranes and flow conditions, according to one or more contemplated embodiments. A reservoir 502 was filled with 20-500 cc of whole blood and provided to the filter module 102 incorporating a filter membrane therein via inlet line 504. Flow exiting the retentate channel was recirculated back to reservoir 502 using pump 510 and recirculating line 508. Flow exiting the permeate channel was directed to a collection container 520 using pump 516 and permeate line 514. At the completion of each test, the composition of fluid in reservoir 502 and collection container 520 were evaluated to determine percentage recovery of spiked tumor cells in the retentate and permeate. Pressures before and after the filter module 102 were monitored by pressure sensors 506 and 512, respectively, while pressure in the permeate channel was monitored by pressure sensor 518. Signals from the pressure sensors 506, 512, 518 were used to monitor transmembrane pressure. Pump flow rates were controlled to be less than the characteristic red blood cell passage rate for a particular filter membrane.

Figure 6:
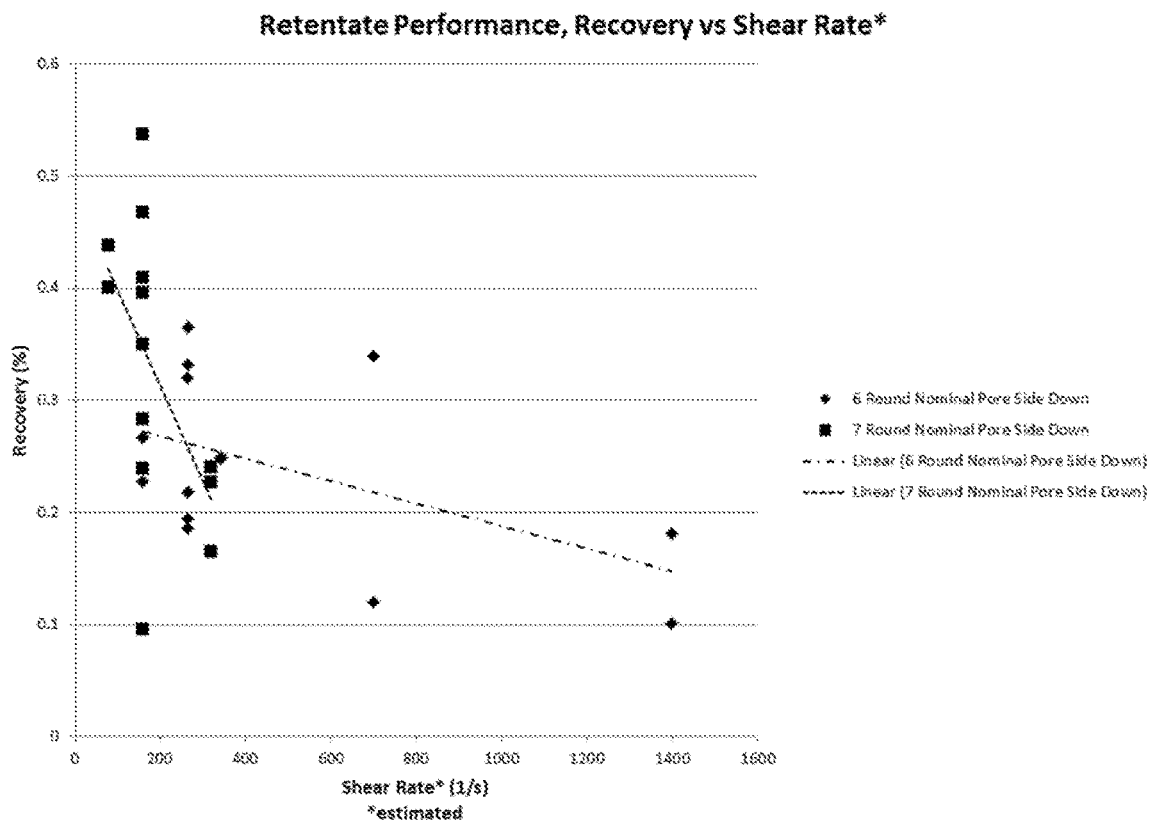
FIG. 6 is a graph of estimated average shear rate through pores of the filter membrane versus recovery of spiked tumor cells in the retentate stream for different filter membranes and flow conditions.
Figure 7:
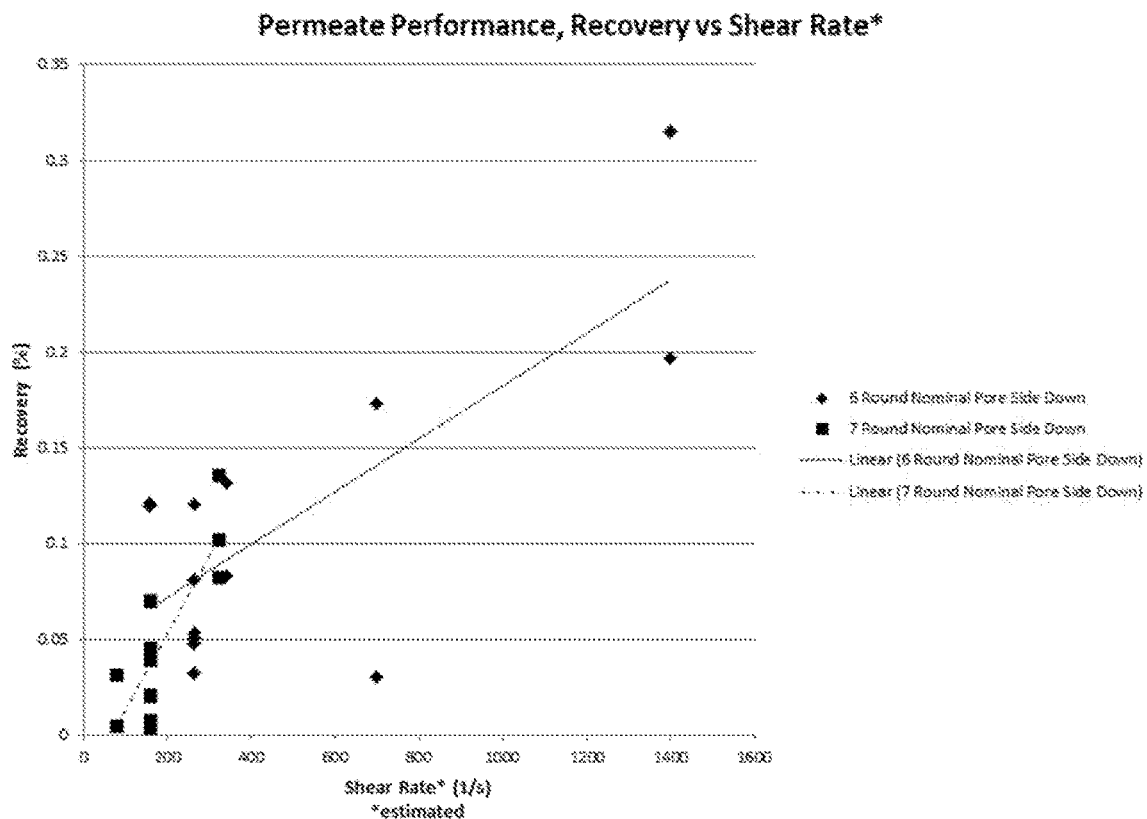
FIG. 7 is a graph of estimated average shear rate through pores of the filter membrane versus recovery of spiked tumor cells in the permeate stream for different filter membranes and flow conditions.

Results of the tests are shown in FIGS. 6-7 and the table below. As is apparent from the data, 6 μm-7 μm diameter pores in an orientation with the nominal pore dimension down (i.e., with the larger diameter end of the pore adjacent to the retentate channel and the nominal diameter end adjacent to the permeate channel), labeled "dimple up" in the table, produce superior results.

In certain embodiments, the cross-flow filter, pumps and channels are sized such that a stable permeate flow of blood (e.g., the fluid depleted of CTCs) is achieved.

In some embodiments, the permeate and/or the retentate flow channel is a rectangular, rhomboidal, or tetrahedral flow channel, or is formed in other similar shapes to provide for a constant shear rate and trans-membrane pressure. In some embodiments, the filter module has a length equivalent to the length of the cross-flow filter contained within the module. In some embodiments, the filter has a length that is at least ten times the channel height or width.

In some embodiments, the retentate fluid flow has a predefined mean shear rate of at least about 100 $s^{-1}$ (e.g., at least about 100 $s^{-1}$, 200 $s^{-1}$, 500 $s^{-1}$, 1000 $s^{-1}$, 2000 $s^{-1}$, or 5000 $s^{-1}$, or any value in between).

TABLE 2

Recovery of Spiked Tumor Cells in Retentate and Permeate Flows for Various Filter Sizes/Orientations.

| Nominal Pore Size (μm) | Orientation | Permeate Pump Speed (ml/min) | RBC/Pore/Sec | Estimated Pore Shear | Initial Spike | Retentate Recovery | Retentate Recovery | Permeate Recovery | Permeate Recovery | Total Capture |
|---|---|---|---|---|---|---|---|---|---|---|
| 4 × 12 Perp | Dimple Up | 0.19 | 25 | 115 | 1.01E+06 | 3.53E+05 | 34.99% | 1.30E+04 | 1.29% | 36.28% |
| 5 × 12 | Dimple Up | 6.2 | 800 | 2370 | 9.86E+05 | 8.40E+04 | 8.52% | 3.61E+05 | 36.62% | 45.15% |
| 5 × 12 | Dimple Up | 3.1 | 400 | 1185 | 9.85E+05 | 6.77E+04 | 6.87% | 3.26E+05 | 33.11% | 39.98% |
| 5 × 12 | Dimple Down | 2.33 | 300 | 889 | 9.85E+05 | 7.25E+04 | 7.36% | 2.59E+05 | 26.26% | 33.62% |
| 5 × 12 | Dimple Down | 1.16 | 150 | 444 | 9.91E+05 | 2.11E+05 | 21.30% | 2.10E+05 | 21.22% | 42.53% |
| 6 Round | Dimple Up | 0.8 | 100 | 699 | 9.85E+05 | 3.35E+05 | 33.96% | 3.01E+04 | 3.06% | 37.02% |
| 6 Round | Dimple Up | 0.8 | 100 | 699 | 1.00E+06 | 1.21E+05 | 12.07% | 1.74E+05 | 17.32% | 29.38% |
| 6 Round | Dimple Up | 1.6 | 200 | 1397 | 1.01E+06 | 1.02E+05 | 10.13% | 3.17E+05 | 31.48% | 41.62% |
| 6 Round | Dimple Up | 1.6 | 200 | 1397 | 1.00E+06 | 1.82E+05 | 18.10% | 1.98E+05 | 19.72% | 37.82% |
| 6 Round | Dimple Up | 0.39 | 49 | 342 | 6.72E+05 | 1.67E+05 | 24.88% | 8.87E+04 | 13.20% | 38.08% |
| 6 Round | Dimple Up | 0.39 | 49 | 342 | 9.86E+05 | 2.45E+05 | 24.86% | 8.18E+04 | 8.29% | 33.15% |
| 6 Round | Dimple Up | 0.3 | 37.5 | 265 | 9.99E+05 | 2.18E+05 | 21.78% | 8.11E+04 | 8.12% | 29.90% |
| 6 Round | Dimple Up | 0.3 | 37.5 | 265 | 1.02E+06 | 3.38E+05 | 33.15% | 3.35E+04 | 3.28% | 36.43% |
| 6 Round | Dimple Up | 0.19 | 23 | 160 | 1.01E+06 | 2.71E+05 | 26.71% | 1.21E+05 | 11.99% | 38.69% |
| 6 Round | Dimple Up | 0.19 | 23 | 160 | 1.00E+06 | 2.28E+05 | 22.81% | 1.22E+05 | 12.14% | 34.95% |
| 6 Round | Dimple Up | 0.3 | 37.5 | 265 | 1.00E+06 | 3.66E+05 | 36.50% | 4.82E+04 | 4.80% | 41.30% |
| 6 Round | Dimple Up | 0.3 | 37.5 | 265 | 1.01E+06 | 1.87E+05 | 18.58% | 5.16E+04 | 5.11% | 23.69% |
| 6 Round | Dimple Up | 0.3 | 37.5 | 265 | 1.02E+06 | 1.97E+05 | 19.44% | 1.23E+05 | 12.07% | 31.51% |
| 6 Round | Dimple Up | 0.3 | 37.5 | 265 | 9.88E+05 | 3.16E+05 | 32.00% | 5.30E+04 | 5.36% | 37.36% |
| 7 Round | Dimple Up | 0.78 | 75 | 321 | 7.59E+05 | 1.25E+05 | 16.45% | 6.27E+04 | 8.26% | 24.71% |
| 7 Round | Dimple Up | 0.39 | 37.5 | 160 | 1.02E+06 | 4.75E+05 | 46.77% | 8.19E+03 | 0.81% | 47.58% |
| 7 Round | Dimple Up | 0.39 | 37.5 | 160 | 1.02E+06 | 5.48E+05 | 53.76% | 4.23E+03 | 0.41% | 54.17% |
| 7 Round | Dimple Up | 0.78 | 75 | 321 | 1.00E+06 | 2.40E+05 | 23.97% | 1.02E+05 | 10.23% | 34.20% |
| 7 Round | Dimple Up | 0.78 | 75 | 321 | 1.00E+06 | 2.27E+05 | 22.68% | 1.36E+05 | 13.60% | 36.28% |
| 7 Round | Dimple Up | 0.39 | 37.5 | 160 | 9.98E+05 | 2.38E+05 | 23.89% | 3.96E+04 | 3.97% | 27.86% |
| 7 Round | Dimple Up | 0.39 | 37.5 | 160 | 1.02E+06 | 4.04E+05 | 39.59% | 2.16E+04 | 2.12% | 41.70% |
| 7 Round | Dimple Up | 0.19 | 18 | 79 | 1.01E+06 | 4.42E+05 | 43.84% | 3.18E+04 | 3.16% | 47.00% |
| 7 Round | Dimple Up | 0.19 | 18 | 79 | 1.01E+06 | 4.05E+05 | 40.07% | 5.09E+03 | 0.50% | 40.58% |
| 7 Round | Dimple Up | 0.3 | 37.5 | 160 | 1.01E+06 | 9.70E+04 | 9.62% | 7.12E+04 | 7.06% | 16.68% |
| 7 Round | Dimple Up | 0.3 | 37.5 | 160 | 1.01E+06 | 3.53E+05 | 35.05% | 4.39E+04 | 4.36% | 39.40% |
| 7 Round | Dimple Up | 0.3 | 37.5 | 160 | 1.02E+06 | 4.16E+05 | 40.90% | 2.07E+04 | 2.04% | 42.94% |
| 7 Round | Dimple Up | 0.3 | 37.5 | 160 | 1.01E+06 | 2.87E+05 | 28.31% | 4.62E+04 | 4.57% | 32.88% |

In some embodiments, the permeate and retentate channels are able to maintain a constant ratio of the transmembrane pressure and the shear rate along the filter membrane.

In some embodiments, the retentate channel has a height between about 50 μm and 500 μm.

Figure 8A:
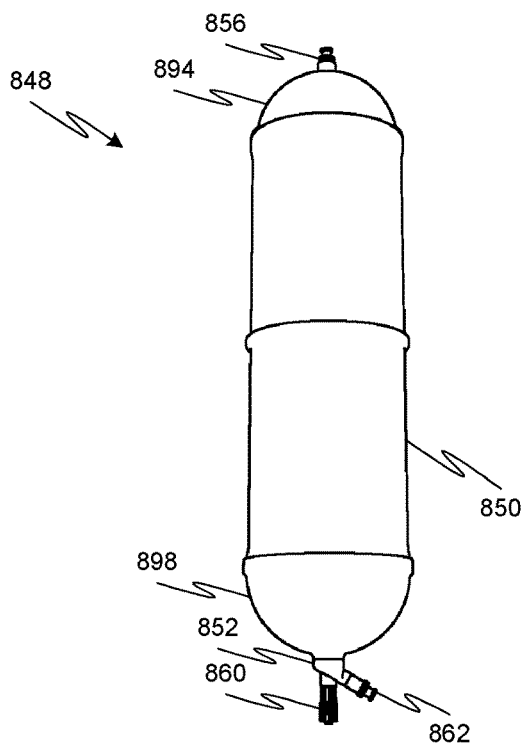

Referring to FIG. 8A, a cylindrical filter module 848 has spherical inlet and outlet transitions 837 and 838 that connect to internal annular retentate 812 channel. The spherical outlet transition 838 further connects to an internal cylindrical permeate channel 833. These are detailed in further drawings. A cylindrical casing 850 is bonded to spherical shells 896 and 855, including an inlet shell 894 with an inlet port 856 and an outlet shell 898 with a permeate outlet port 862 and a retentate port 860. An annular hub 852 defines a retentate channel that guides permeate flow smoothly toward the permeate outlet port 862. The inlet port 856, retentate port 860, and the permeate outlet port 862 may all have connectors for fluid lines.

FIGS. 8B, 8C, and 8D show details of the filter of FIG. 8A. Blood flows into inlet port 856 and passes through a spherical channel 827 defined between an inner surface 835 of an outer spherical cap 894 and the outer surface 832 of an inner spherical cap 876. The channel 827 connects to an annular retentate channel 812 defined between a cylindrical core 866 and an annular filter membrane 880. Permeate flows through the filter membrane 880 into an annular permeate channel 833 defined between the annular filter membrane 880 and the cylindrical casing 850. After passing through the annular permeate channel 833, permeate is conveyed through a spherical permeate transition channel 839 defined between the outer surface of a spherical liner cap 890 and the inner surface of the outlet shell 898. The outlet shell has an annular hub 852 that collects and guides blood flow to the permeate outlet port 860. The spherical permeate transition channel 814 is defined between the inner spherical cap 876 outer surface 877 and an inner surface 879 of a spherical liner cap 890. The retentate is conveyed through a spherical retentate transition channel 875 defined between the inner surface 816 of the spherical liner cap 890 and the outer surface of the inner spherical cap 876 and then flows into an outlet channel 862 that passes through the center of the annular hub 820.

It will be observed that all of the channels have substantially uniform depths so that there are no dead spaces where coagulation might be promoted. Further, the depth of the transitions are selected to maintain the levels of shear described including in the transitions to ensure uniform distribution due to the substantial pressure change in the blood flow through the transitions. The cylindrical arrangement of the filter membrane also helps to ensure precisely defined spacing due to the fact that the filter membrane may be of high tensile strength material and is formed in cylinder providing the benefit of the inherent "hoop strength" of this configuration. The retentate channel, in use, is under pressure due to the transmembrane pressure between the retentate and permeate channels. So the filter membrane remains in a defined shape and dimension within the outer casing 850 and the core 866. Further, the depth of the retentate channel is able to made uniform further owing to the hoop strength and tensile strength of the filter membrane. Example embodiments may be between 12 and 18 inches in length and about 3-6 inches in diameter. The diameter may be chosen to ensure against creasing of the filter membrane during manufacture and shipping. The cylindrical filter module 848 shape also lends itself to compact design with a shape that is familiar to blood oxygenators and dialyzers.

Figure 9A:
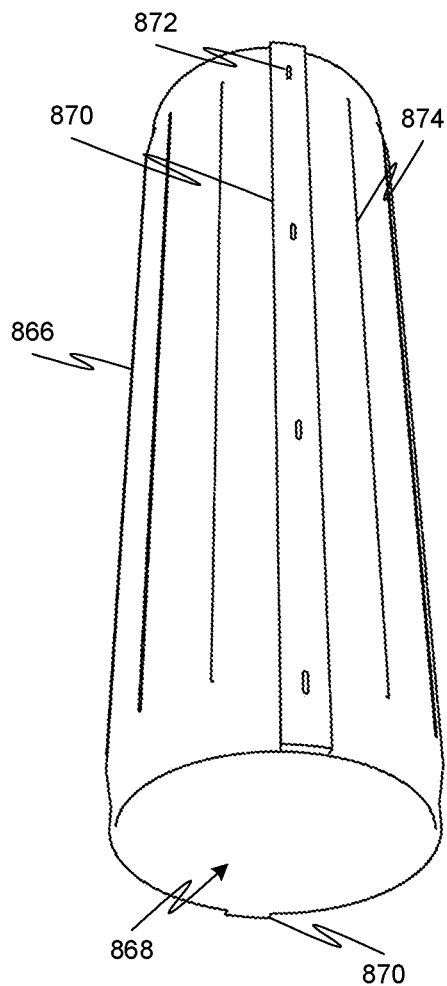
Figure 9B:
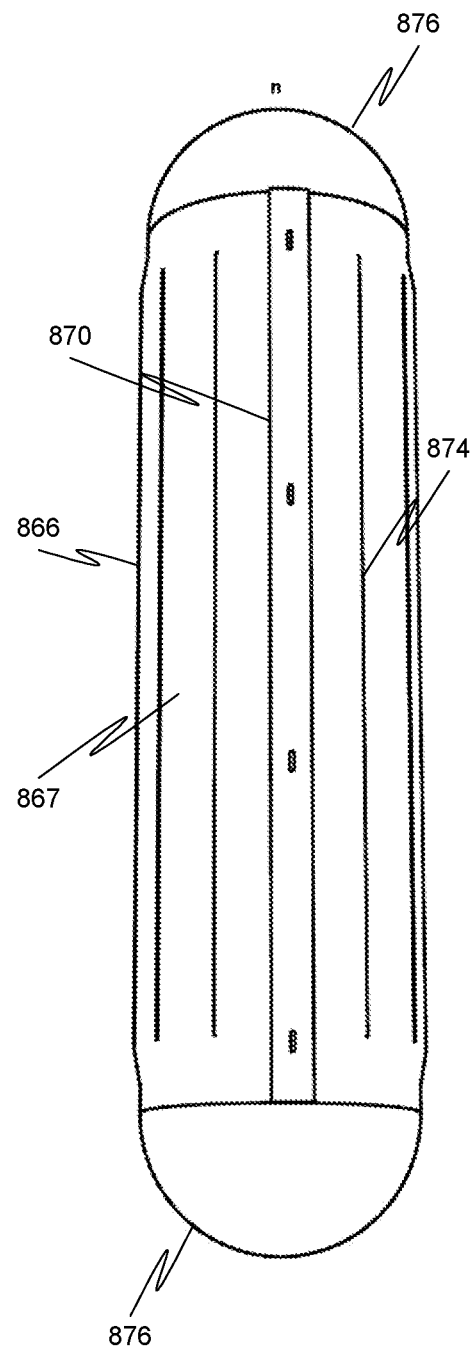

FIGS. 9A-9H, 9J-9N and 9P show the features of the cylindrical filter module 848 including various steps during the process of assembly. The assembly process may vary from what is shown but the stages help to clarify the structure of the 848 and show features that may be advantageous in any method of assembly. Referring to FIGS. 9A and 9B, the cylindrical core 866 has minor ribs 874 that provide rigidity and act as spacers to support the annular filter membrane 880 and maintain a depth of the annular retentate channel 812. Two major ribs 870 on opposite sides of the cylindrical core 866 have bosses 872 that act as guides for the cylindrical casing 850 when it is emplaced thereover. The bosses 872 also help to guide assembly of the annular filter membrane 880. The inner spherical caps 876 fit into the opposite ends of the cylindrical core 866 providing a smooth continuous surface 867 over which the retentate flows between the flows into flows into inlet port 856 and retentate outlet port 860. Thus, the structure of FIG. 9B shows the entire inner surface of the retentate channel from one end of the structure of the 848 to the other.

Figures 9C, 9D:
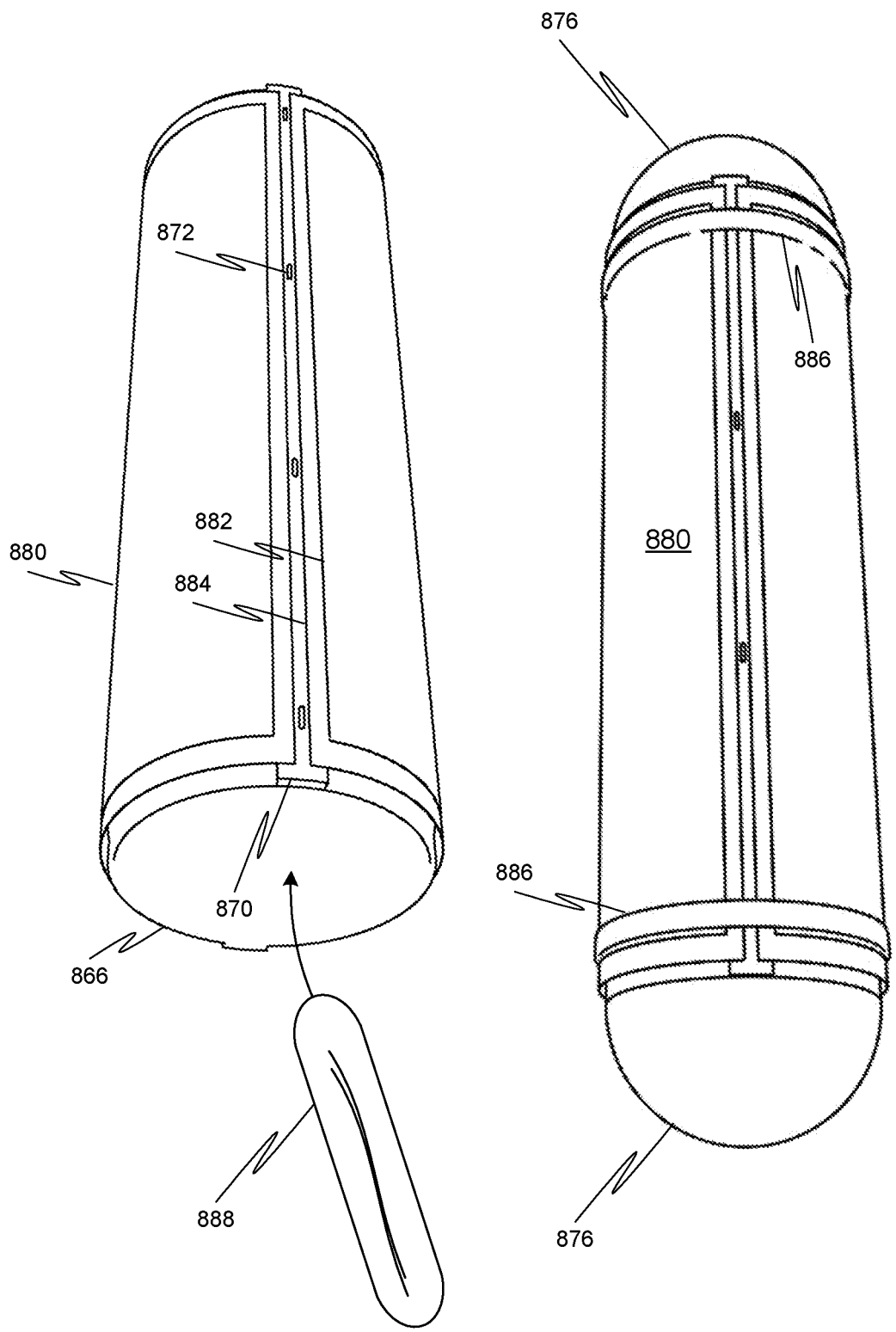

The inner spherical caps 876 are not emplaced initially and are only shown in position for purposes of description. The first step in assembly is shown in FIG. 9C in which a single annular filter membrane 880 is wrapped around the cylindrical core 866. The annular filter membrane 880 has a region 882 that stops near its outer edge 884, the space between them having no pores and the region including a main central region of the annular filter membrane 880 that has pores. Before wrapping the annular filter membrane 880 around the cylindrical core 866, ultraviolet-curable adhesive (e.g., acrylic) is applied to one or both of the major ribs 870 and edges of the annular filter membrane 880. The cylindrical core 866 is wrapped in a mildly taught manner over the major ribs 870 and held in position while a ultraviolet lamp 888 is placed in the center. The cylindrical core 866 is transparent to ultraviolet thereby allowing the adhesive to be cured quickly by irradiating from the inside of the cylindrical core 866.

In FIG. 9D, once the adhesive is cured, the inner spherical caps 876 may be emplaced and bonded to the cylindrical core 866 and retention rings 886 emplaced around the subassembly that includes the positioned annular filter membrane 880. The inner spherical caps 876 may be bonded with adhesive or friction welded or any other suitable method may be used. The placement of the retention rings is more inward (toward the center longitudinally) than their final placement to facilitate the next step shown in FIGS. 9E and 9D.

Figures 9E, 9F, 10:
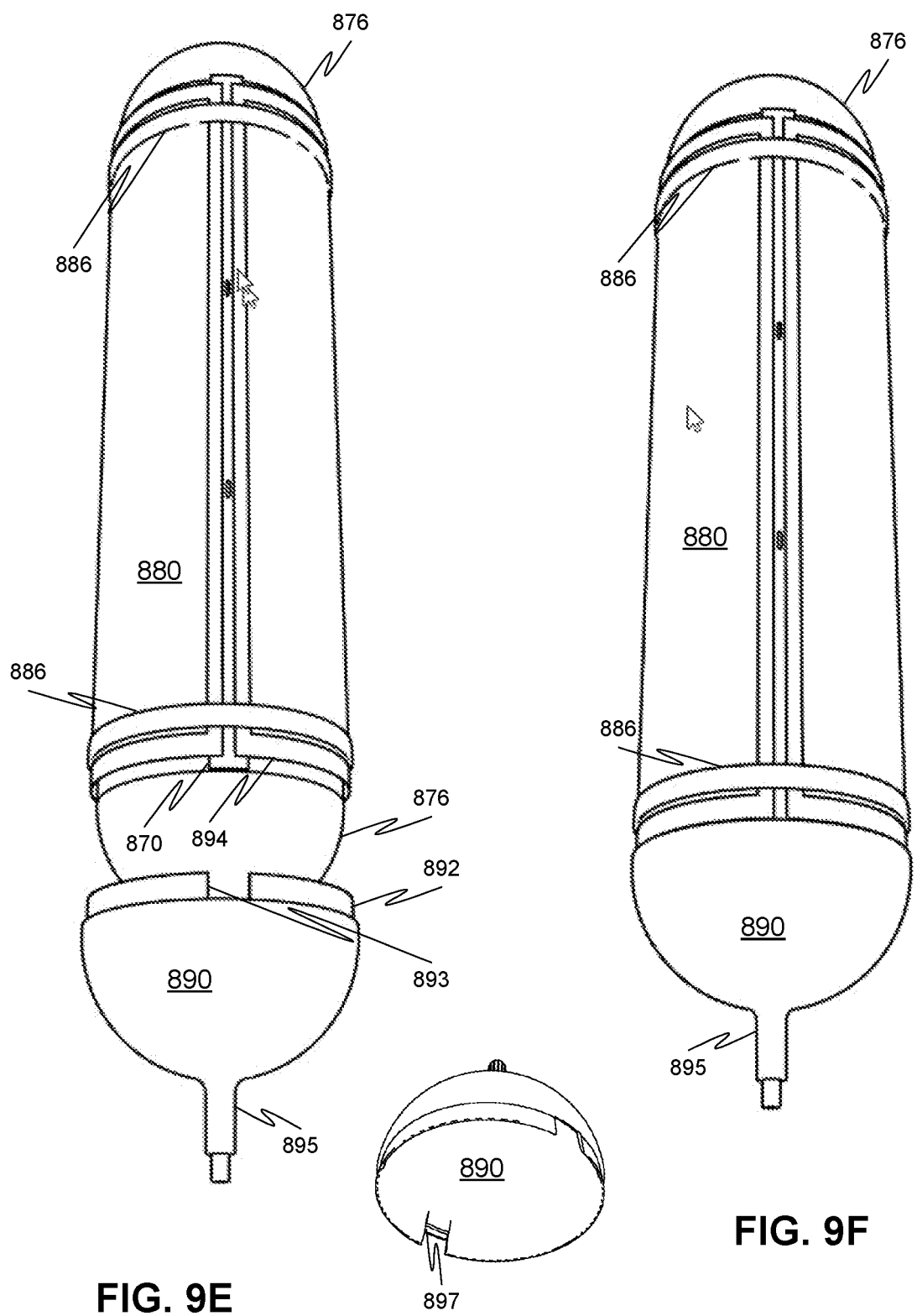

Referring to FIGS. 9E and 9F, the spherical liner cap 890 discontinuous rim 892 is fitted underneath the annular filter membrane 880. The discontinuous rim 892 fits underneath the annular filter membrane 880. Once positioned it largely floats or hovers over the inner spherical caps 876 but it also registers in engagement with the major ribs 870 that fit into slots 897 formed inside the spherical liner cap 890 as shown in FIG. 10. Ultimately, when the outlet shell 898 is installed and affixed to the annular filter membrane 880, the spherical liner cap 890 is further supported by a neck 895 that fits snuggly in the annular hub 852 which, as may be confirmed by inspection, leaves no rotational degrees of freedom for the spherical liner cap 890 to be displaced. Note that certain curves in the drawing of FIG. 10 appear as broken lines, but this is rendering artifact and not a feature of the spherical liner cap 890.

Figure 9G:
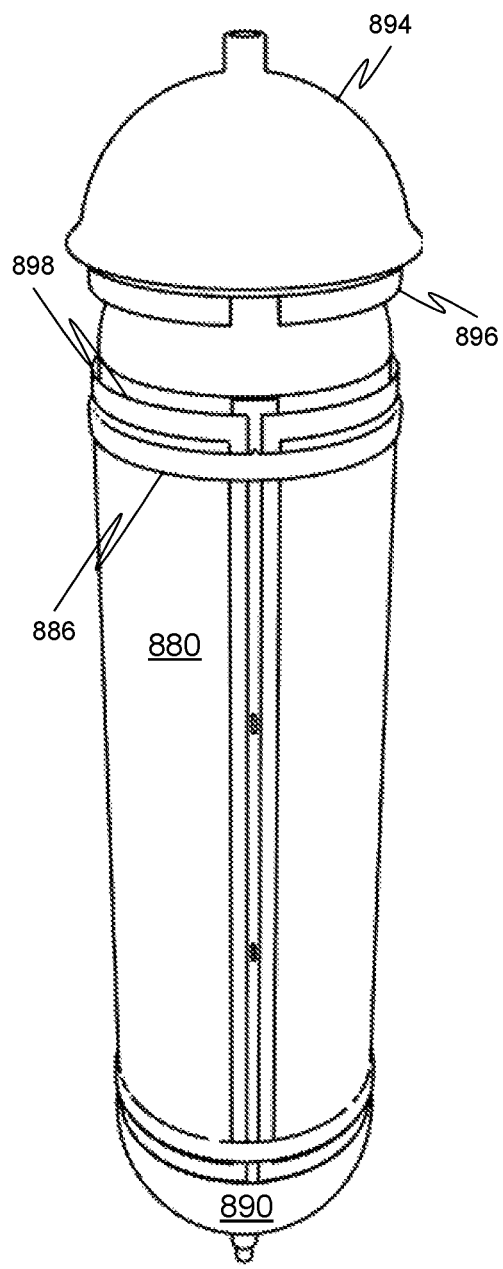
Figure 9H:
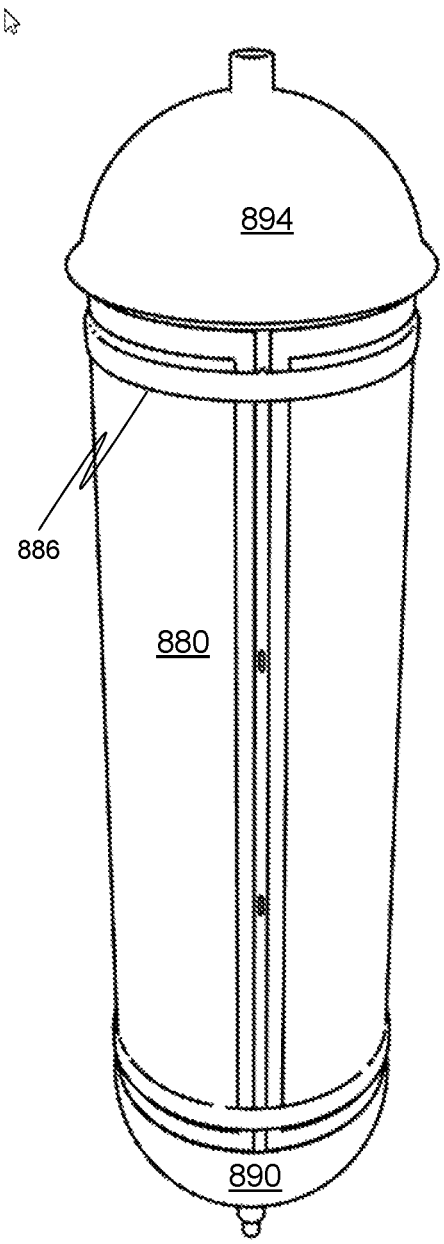
Figure 9J:
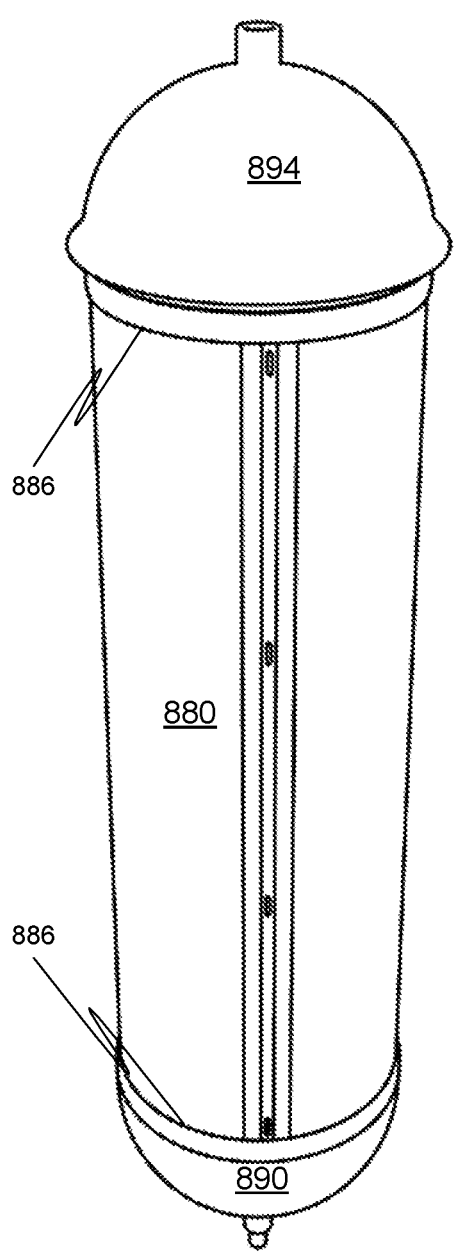

Referring now to FIGS. 9G and 9H, the outer spherical cap 894 has a discontinuous rim 896 that is inserted in a similar matter under the edge of the annular filter membrane 880 at the inlet end of the filter module. The outer spherical cap 894 has the same slots as indicated at 897 to engage the major ribs 870 to help support the outer spherical cap 894. Referring now to FIG. 9J, the retention rings 886 are slid toward outer spherical cap 894 and spherical liner cap 890 respectively, securely gripping the edges of the annular filter membrane 880 between a respective retention ring 886 and the respective one of the discontinuous rim 896 and discontinuous rim 892.

Figure 9K:
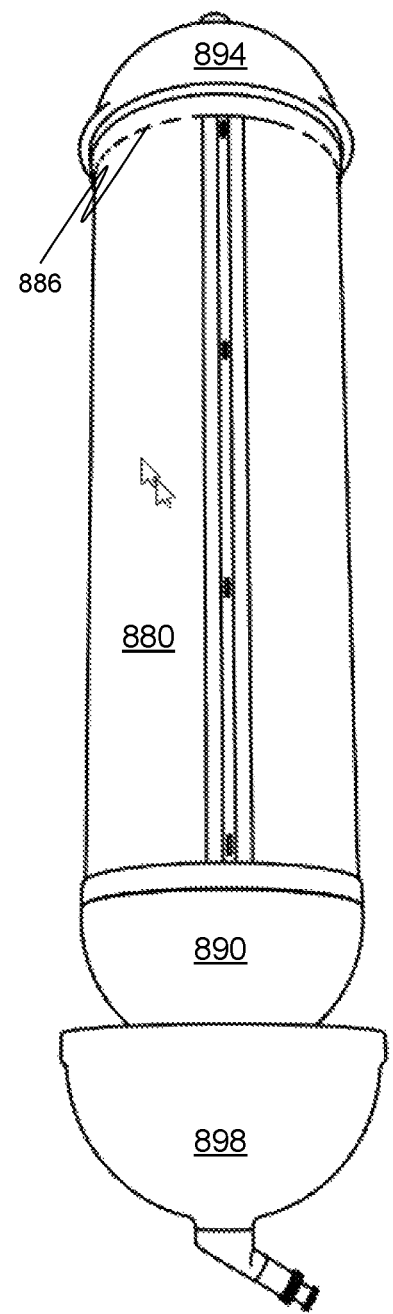
Figures 9L, 9M:
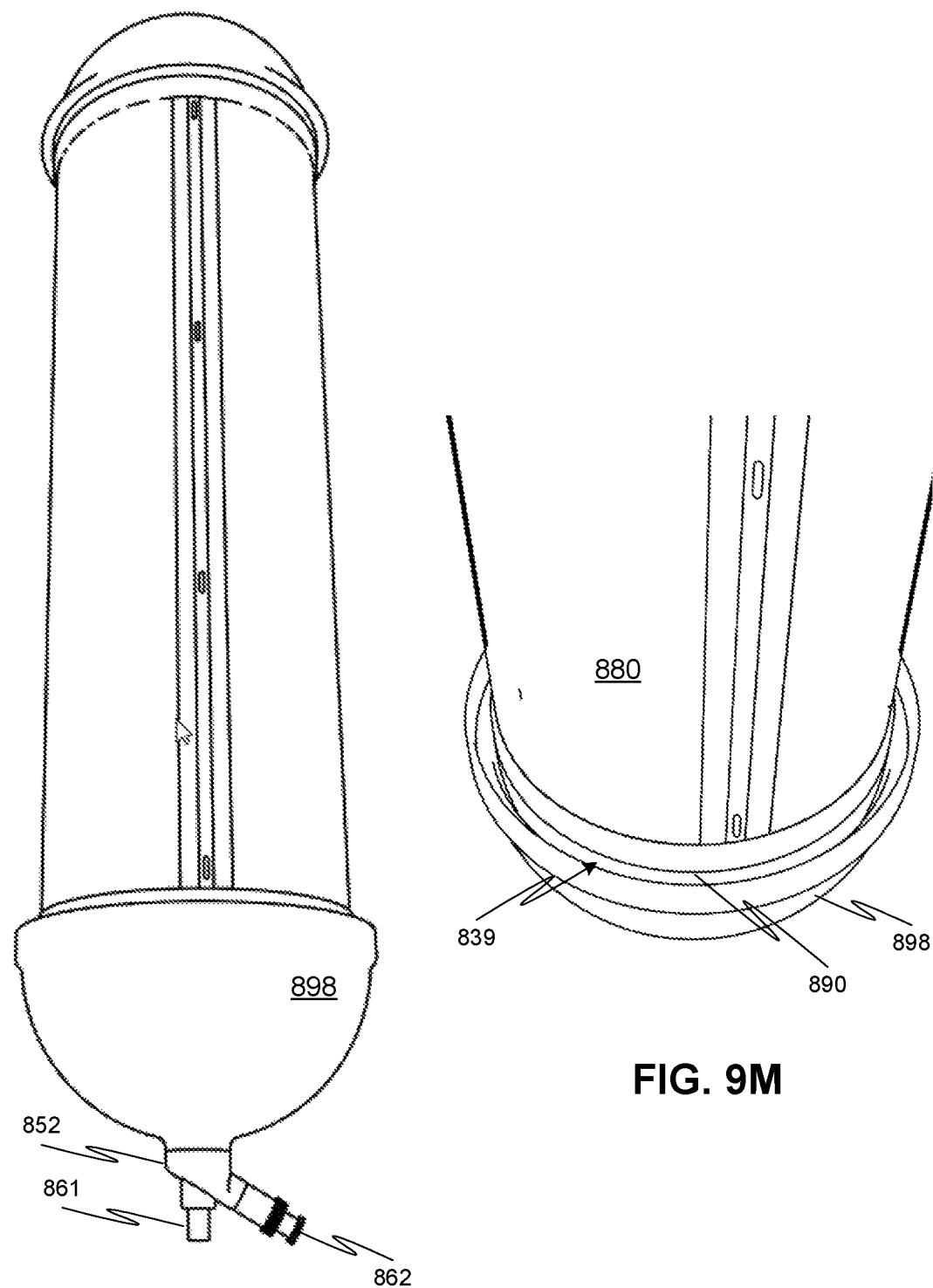

Referring now to FIGS. 9K, 9L, and 9M, the outlet shell 898 is shown being positioned temporarily in place adjacent the spherical liner cap 890 to allow a view of how a spherical permeate transition channel 839 is formed between the spherical liner cap 890 and the outlet shell 898. In assembly, since the outlet shell 898 attaches to the cylindrical casing 850, the latter is emplaced first and then the 898 is positioned and attached to it as shown in FIGS. 9N and 9P. The cylindrical casing 850 is axially aligned with the previously assembled components which are inserted into the cylindrical casing 850. Then the then the 898 is positioned and both the outer spherical cap 894 and then the 898 bonded to the cylindrical casing 850 to complete the major aspects of the assembly. The retentate outlet is form in the spherical liner cap 890 and is guided through an opening in the then the then the 898 annular hub 852 forming a seal. Fittings for the inlet port 856 and outlet channel 862 may be attached.

Other methods of manufacturing are possible. For example, the transitions could be 3D printed rather than assembled as shown. A radial stack of ring spacers may be positioned over the core with a sheet of the filter membrane, rolled into a tube, sandwiched between them. Heating and cooling in place may be sufficient to form a seal over a rigid cored to which the transitions may be attached. In this way, the hoop strength of the cylindrical form of the filter membrane and the outer and inner walls can still provide the precise spacing and resistance to pressure as the fully cylindrical shape of the above embodiments. Other configurations are also feasible. For example, as shown in FIG. 11, a strong reusable plate 918 with slots 928 to receive the ends of an inner shell 922, an outer shell 926, and a filter membrane 924. The latter three elements may be disposable. The ends may be held fast by means of a spacer 932 and a wedge 930 and the retentate and permeate channels between them may be hermetically sealed so that the three inner shell 922, an outer shell 926, and a filter membrane 924 can be delivered as a pre-sterilized disposable unit. Headers may be 3D printed to interface with the inner shell 922, an outer shell 926, and a filter membrane 924. Also in this embodiment and in others, multiple layers of permeate and retentate channels as well as filter membranes dividing them may be provided to occupy the space at different radial distances from an axis of the configuration.

The filter module 848 and other embodiments provide a rigid inner wall that withstands compression forces due to retentate channel pressure, a filter membrane with high elastic modulus to withstand outward pressure of the retentate channel and a rigid outer wall that withstands outward pressure of the permeate channel. The resistance to the pressure provides low deformation but also any deformation is uniformly distributed so that the depth of the retentate and permeate channels can be controlled and thereby ensure that effective shear rates are maintained. The flow transitions may be used but the spherical shape is also particularly adapted for ensuring that the spacing between the channel walls is controllable. Preferably in the transitions, which are dome shaped, the channels are deeper near the apex (inlet and outlet) since the circumferences of the channels are smaller there.

In one or more first embodiments, a method of removing circulating tumor cells (CTCs) from whole blood comprises flowing the whole blood along a retentate channel of a cross-flow module. A wall of the retentate channel is formed by a first surface of a filter membrane. The filter membrane separates the retentate channel from a permeate channel of the cross-flow module. The filter membrane is arranged parallel to a direction of fluid flow through the retentate channel. A wall of the permeate channel is formed by a second surface of the filter membrane opposite to the first surface. The method further comprises, at the same time as the flowing along the retentate channel, flowing fluid along the permeate channel, which fluid has passed through the filter membrane into the permeate channel and includes at least red blood cells from the whole blood. The method further comprises controlling a flow rate of the flowing along the retentate channel and/or a flow rate of the flowing along the permeate channel such that a per-pore flow rate of red blood cells through the filter membrane is less than a characteristic red blood cell passage rate for said filter membrane. The filter membrane has an array of tapered pores extending from one of the first and second surfaces to the other of the first and second surfaces. Each pore has a first cross-width dimension at said one of the first and second surfaces of the filter membrane greater than a nominal cross-width dimension at said other of the first and second surfaces of the filter membrane. Each pore is sized to obstruct passage of CTCs therethrough.

In the first embodiments or any other embodiment, each pore has the first cross-width dimension at the first surface of the filter membrane that is greater than the nominal cross-width dimension at the second surface of the filter membrane.

In the first embodiments or any other embodiment, each pore has the first cross-width dimension at the second surface of the filter membrane that is greater than the nominal cross-width dimension at the first surface of the filter membrane.

In the first embodiments or any other embodiment, the fluid having passed through the filter membrane into the permeate channel includes at least red blood cells, platelets, and white blood cells from the whole blood.

In the first embodiments or any other embodiment, the characteristic red blood cell passage rate through the pores is that attending a maximum flow rate of washed red blood cells, with a hematocrit of at least 10% (e.g., 10%, 30%, 35%, 40%, 45%, 50%, or any other value between 10% and 50%), that is effective for continuously flowing with less than a 100 torr rise in transmembrane pressure over a four hour timeframe.

In the first embodiments or any other embodiment, the characteristic red blood cell passage rate corresponds to an average shear rate through the pores of the filter membrane that is less than 350 $s^{-1}$ for circular pores having a nominal diameter in a range of 5.5-7.5 μm.

In the first embodiments or any other embodiment, the characteristic red blood cell passage rate corresponds to an average shear rate through the pores of the filter membrane of 160 $s^{-1}$.

In the first embodiments or any other embodiment, the retentate channel has a height that tapers from a first height at an upstream end of the retentate channel to a second height at a downstream end of the retentate channel, and the second height is less than the first height.

In the first embodiments or any other embodiment, each pore has a circular cross-section with a nominal diameter at the other of the first and second surfaces of 4-8 μm, inclusive.

In the first embodiments or any other embodiment, each pore has an axially-extending portion with a constant diameter, and a length of the constant-diameter axially-extending portion is less than 1 μm.

In the first embodiments or any other embodiment, each pore has an axially-extending portion with a constant diameter, and a length of the constant-diameter axially-extending portion is in a range of 1-10 μm.

In the first embodiments or any other embodiment, the filter membrane has a thickness between the first and second surfaces of 1-50 μm, inclusive.

In the first embodiments or any other embodiment, each pore is linearly tapered at angle of 11°±3° with respect to a corresponding axis thereof.

In the first embodiments or any other embodiment, the flowing along the retentate channel and the flowing along the permeate channel are controlled such that shear rate at each point across the first surface of the filter membrane is greater than a first value for adequate sweeping of the first surface and less than a second value associated with hemolysis.

In the first embodiments or any other embodiment, the first value is a shear rate of 500 $s^{-1}$, and the second value is a shear rate of 1000 $s^{-1}$.

In the first embodiments or any other embodiment, the flowing along the retentate channel and the flowing along the permeate channel are controlled such that shear rate at each point across the first surface of the filter membrane is greater than an average shear rate through the pores of the filter membrane.

In the first embodiments or any other embodiment, the average shear rate through the pores of the filter membrane is 160 $s^{-1}$ or less.

In the first embodiments or any other embodiment, the filter membrane is formed of a polymer.

In the first embodiments or any other embodiment, the polymer comprises polyimide, polyethylene terephthalate, or polycarbonate.

In the first embodiments or any other embodiment, the method further comprises using laser machining to form a uniform array of pores in a polymer sheet to produce the filter membrane, and installing the filter membrane in the cross-flow module between the retentate and permeate channels.

In the first embodiments or any other embodiment, the method further comprises at a same time as the flowing along the retentate channel, recirculating fluid from an outlet end of the retentate channel to an inlet end of the retentate channel upstream from the filter membrane.

In the first embodiments or any other embodiment, the recirculating is by way of an accumulation chamber arranged upstream from the inlet end of the retentate channel.

In the first embodiments or any other embodiment, the accumulation chamber has a volume in a range of 5-500 ml, inclusive.

In the first embodiments or any other embodiment, the method further comprises flowing whole blood from a patient to the accumulation chamber. The flowing fluid along the permeate channel includes injecting the fluid from the permeate channel back into the patient.

In the first embodiments or any other embodiment, the method further comprises adding a regional anticoagulant to the whole blood prior to the cross-flow module.

In the first embodiments or any other embodiment, the flowing whole blood from the patient and the injecting the fluid back into the patient are at the same flow rate.

In the first embodiments or any other embodiment, the flowing whole blood from the patient is at a flow rate in a range of 5-80 ml/min, inclusive.

In the first embodiments or any other embodiment, the flowing along the retentate channel and the flowing along the permeate channel are performed for at least one hour continuously while maintaining flow conditions that hold a transmembrane pressure rise for the filter membrane to less than or equal to 100 torr.

In the first embodiments or any other embodiment, the flowing along the retentate channel and the flowing along the permeate channel are performed for a time period necessary to filter 5 liters of whole blood without a transmembrane pressure rise for the filter membrane exceeding 100 torr.

In one or more second embodiments, a method of removing circulating tumor cells (CTCs) from whole blood comprises, for at least an hour, continuously flowing whole blood along and parallel to a first side of a filter membrane while withdrawing filtrate that has passed through to a second side of the filter membrane opposite the first side such that red blood cells from the whole blood pass through the filter membrane without a rise in transmembrane pressure exceeding 100 torr over the at least an hour. The filter membrane has an array of pores. Each pore tapers with respect to a thickness direction of the filter membrane from one of the first and second sides to the other of the first and second sides. Said one of the first and second sides has a greater open area than said other of the first and second sides of the filter membrane.

In the second embodiments or any other embodiment, each pore tapers with respect to the thickness direction from the first side to the second side such that the first side has a greater open area than the second side of the filter membrane.

In the second embodiments or any other embodiment, each pore tapers with respect to the thickness direction from the second side to the first side such that the second side has a greater open area than the first side of the filter membrane.

In the second embodiments or any other embodiment, the array of pores is sized so as to obstruct passage of CTCs therethrough.

In the second embodiments or any other embodiment, the continuously flowing whole blood and withdrawing filtrate are such that an average shear rate through the pores of the filter membrane is less than 350 $s^{-1}$ for circular pores having a minimum diameter in a range of 5.5-7.5 µm.

In the second embodiments or any other embodiment, the continuously flowing whole blood and withdrawing filtrate are such that a shear rate at each point across the first surface of the filter membrane is between 500 $s^{-1}$ and 1000 $s^{-1}$.

In the second embodiments or any other embodiment, the continuously flowing whole blood and withdrawing filtrate are such that shear rate at each point across the first surface of the filter membrane is greater than an average shear rate through the pores of the filter membrane.

In the second embodiments or any other embodiment, the average shear rate through the pores is 160 $s^{-1}$ or less.

In the second embodiments or any other embodiment, the filter membrane is formed of a polymer.

In the second embodiments or any other embodiment, the method further comprises removing the whole blood from a patient for said continuously flowing while infusing the withdrawn filtrate into the patient's vascular system as part of a cancer therapy.

In the second embodiments or any other embodiment, the removing the whole blood and/or the infusing is at a flow rate in a range of 5-80 ml/min, inclusive.

In the second embodiments or any other embodiment, the continuously flowing whole blood and withdrawing filtrate are performed for at least four hours without the transmembrane pressure rise exceeding 100 torr.

In the second embodiments or any other embodiment, the continuously flowing whole blood and withdrawing filtrate are sufficient to process 5 liters of whole blood in a single continuous treatment session.

In one or more third embodiments, a system for removing circulating tumor cells (CTCs) from whole blood comprises at least a cross-flow module and a controller that controls flows to/from the cross-flow module. The system can be configured to perform the method of any of the first and second embodiments, or any other embodiment.

In one or more fourth embodiments, a system for removing circulating tumor cells (CTCs) from whole blood comprises a cross-flow module and a controller. The cross-flow module has a retentate channel, a permeate channel, and a filter membrane. The filter membrane separates the retentate channel from the permeate channel and is arranged parallel to a direction of fluid flow through the retentate channel. The filter membrane further has an array of tapered pores extending through the filter membrane. Each pore has a cross-width dimension that narrows from one of the retentate and permeate channels to the other of the retentate and permeate channels. The controller is configured to control at least a flow rate of whole blood through the retentate channel and/or a flow rate of fluid along the permeate channel responsively to a signal indicative of a rise in transmembrane pressure of the filter membrane.

In the fourth embodiments or any other embodiment, the cross-width dimension of each pore narrows from the retentate channel to the permeate channel.

In the fourth embodiments or any other embodiment, the cross-width dimension of each pore narrows from the permeate channel to the retentate channel.

In the fourth embodiments or any other embodiment, the controller is configured to control the flow rates such that the rise in transmembrane pressure is less than or equal to 100 torr.

In the fourth embodiments or any other embodiment, the controller is configured to control the flow rates such that the average flow rate through the pores of the filter membrane is less than a characteristic red blood cell passage rate for the filter membrane. The characteristic red blood cell passage rate is that attending a maximum flow rate of washed red blood cells, with a hematocrit of at least 10% (e.g., 10%, 30%, 35%, 40%, 45%, 50%, or any other value between 10% and 50%), that is effective for continuously flowing with less than a 100 torr rise in transmembrane pressure over a four hour timeframe.

In the fourth embodiments or any other embodiment, the controller is configured to control the flow rates such that the average flow rate through the pores of the filter membrane is less than 350 $s^{-1}$ for circular pores having a minimum diameter in a range of 5.5-7.5 µm.

In the fourth embodiments or any other embodiment, the retentate channel has a height that tapers from a first height at an upstream end of the retentate channel to a second height at a downstream end of the retentate channel. The second height is less than the first height.

In the fourth embodiments or any other embodiment, each pore has a minimum diameter in a range of 4-8 µm, inclusive.

In the fourth embodiments or any other embodiment, each pore has an axially-extending portion with a constant diameter, and a length of the constant-diameter axially-extending portion is less than 1 µm.

In the fourth embodiments or any other embodiment, each pore has an axially-extending portion with a constant diameter, a length of the constant-diameter axially-extending portion is in a range of 1-10 µm.

In the fourth embodiments or any other embodiment, each pore is linearly tapered at angle of 11°±3° with respect to a corresponding axis thereof.

In the fourth embodiments or any other embodiment, the filter membrane is formed of a polymer.

In the fourth embodiments or any other embodiment, the polymer comprises polyimide, polyethylene terephthalate, or polycarbonate.

In the fourth embodiments or any other embodiment, the system further comprises a recirculating channel and an accumulation chamber. The recirculating channel is coupled to an outlet end of the retentate channel to convey fluid therefrom. The accumulation chamber holds a volume of whole blood therein. The accumulation chamber is coupled to the recirculating channel to receive fluid therefrom and to an inlet end of the retentate channel to convey fluid thereto.

In the fourth embodiments or any other embodiment, the accumulation chamber has a volume in a range of 5-500 ml, inclusive.

In the fourth embodiments or any other embodiment, the system comprises first and second pumps. The first pump conveys fluid from the outlet end of the retentate channel to the accumulation chamber. The second pump conveys fluid from an outlet end of the permeate channel. The controller is configured to control the flow rate of whole blood through the retentate channel and the flow rate of fluid along the permeate channel by controlling the first and second pumps.

In the fourth embodiments or any other embodiment, the system further comprises first through third pressure sensors. The first pressure sensor is disposed (or measures pressure) upstream of an inlet end of the retentate channel. The second pressure sensor is disposed (or measures pressure) downstream of an outlet end of the retentate channel. The third pressure sensor is disposed (or measures pressure) downstream of an outlet end of the permeate channel. The signal indicative of a rise in the transmembrane pressure is based on one or more signals from the first through third pressure sensors.

In the fourth embodiments or any other embodiment, the retentate and permeate channels are cylindrical channels, and the filter membrane is cylindrical with the tapered pores extending from a radially inner circumferential surface to a radially outer circumferential surface.

One or more fifth embodiments include a crossflow filter. A rigid cylindrical inner wall and a rigid cylindrical outer wall inner are axially aligned with the inner wall inside the outer wall. An inelastic filter membrane is positioned between the inner and outer walls defining a retentate channel inside the filter membrane and a permeate channel outside the filter membrane. Transition channels are shaped and connected to the inner and outer walls to deliver a flow of fluid from an inlet port to the retentate channel and to capture flow flowing longitudinally along the cylindrical inner and outer walls from both the retentate and permeate channels to respective outlet ports.

The fifth embodiments can be modified to form additional fifth embodiments in which the inner wall has ribs that span a depth of the retentate channel. The fifth embodiments can be modified to form additional fifth embodiments in which the transition channels are spherical in shape. The fifth embodiments can be modified to form additional fifth embodiments in which the filter membrane is a polymer sheet with a regular array of pores extending through the filter membrane. The fifth embodiments can be modified to form additional fifth embodiments in which the filter membrane is formed by laser drilling the pores. The fifth embodiments can be modified to form additional fifth embodiments in which the filter membrane is a polyimide sheet with a regular array of tapered pores extending through the filter membrane.

The fifth embodiments can be modified to form additional fifth embodiments in which the filter membrane is a polyimide sheet with a regular array of rectangular pores extending through the filter membrane. The fifth embodiments can be modified to form additional fifth embodiments in which filter membrane is a polyimide sheet with a regular array of rectangular pores extending through the filter membrane, the rectangular pores each having a long dimension and a short, wherein the long dimension of each pore is aligned with an axis of the outer wall. The fifth embodiments can be modified to form additional fifth embodiments in which the filter membrane is a polyimide sheet with a regular array of rectangular pores extending through the filter membrane, the rectangular pores each having a long dimension and a short, wherein the short dimension of each pore is aligned with an axis of the outer wall. The fifth embodiments can be modified to form additional fifth embodiments in which each pore has an axially-extending portion with a constant diameter, a length of the constant-diameter axially-extending portion being in a range of 1-10 µm.

The fifth embodiments can be modified to form additional fifth embodiments in which each pore has a minimum diameter in a range of 4-8 µm, inclusive. The fifth embodiments can be modified to form additional fifth embodiments in which each pore has an axially-extending portion with a constant diameter, a length of the constant-diameter axially-extending portion being less than 1 µm. The fifth embodiments can be modified to form additional fifth embodiments in which each pore has an axially-extending portion with a constant diameter, a length of the constant-diameter axially-extending portion being in a range of 1-10 µm. The fifth embodiments can be modified to form additional fifth embodiments in which each pore has a minimum diameter in a range of 4-8 µm, inclusive. The fifth embodiments can be modified to form additional fifth embodiments in which each pore has an axially-extending portion with a constant diameter, a length of the constant-diameter axially-extending portion being less than 1 µm.

The fifth embodiments can be modified to form additional fifth embodiments in which each pore has an axially-extending portion with a constant diameter, a length of the constant-diameter axially-extending portion being in a range of 1-10 µm. The fifth embodiments can be modified to form additional fifth embodiments in which each pore has a minimum diameter in a range of 4-8 µm, inclusive. The fifth embodiments can be modified to form additional fifth embodiments in which each pore has an axially-extending portion with a constant diameter, a length of the constant-diameter axially-extending portion being less than 1 µm. The fifth embodiments can be modified to form additional fifth embodiments in which each pore has an axially-extending portion with a constant diameter, a length of the constant-diameter axially-extending portion being in a range of 1-10 µm. The fifth embodiments can be modified to form additional fifth embodiments in which each pore has a minimum diameter in a range of 4-8 µm, inclusive. The fifth embodiments can be modified to form additional fifth embodiments in which each pore has an axially-extending portion with a constant diameter, a length of the constant-diameter axially-extending portion being less than 1 µm. The fifth embodiments can be modified to form additional fifth embodiments in which each pore has an axially-extending portion with a constant diameter, a length of the constant-diameter axially-extending portion being in a range of 1-10 µm.

The fifth embodiments can be modified to form additional fifth embodiments in which each pore has a minimum diameter in a range of 4-8 µm, inclusive. The fifth embodiments can be modified to form additional fifth embodiments in which each pore has an axially-extending portion with a constant diameter, a length of the constant-diameter axially-extending portion being less than 1 µm. The fifth embodiments can be modified to form additional fifth embodiments in which each pore has an axially-extending portion with a constant diameter, a length of the constant-diameter axially-extending portion being in a range of 1-10 µm. The fifth embodiments can be modified to form additional fifth embodiments in which each pore has a minimum diameter in a range of 4-8 µm, inclusive. The fifth embodiments can be modified to form additional fifth embodiments in which each pore has an axially-extending portion with a constant diameter, a length of the constant-diameter axially-extending portion being less than 1 µm. The fifth embodiments can be modified to form additional fifth embodiments in which the polymer is one of polyimide, polyethylene terephthalate, and polycarbonate. The fifth embodiments can be modified to form additional fifth embodiments in which the inner and outer walls are of polymer.

The fifth embodiments can be modified to form additional fifth embodiments that include a sterile container housing the filter, the filter being sterile and sealed within the sterile container. The fifth embodiments can be modified to form additional fifth embodiments in which the ports are configured to withstand a pressure of at least 200 torr. The fifth embodiments can be modified to form additional fifth embodiments in which the transition channels each have a rim that supports an edge of the filter membrane. The fifth embodiments can be modified to form additional fifth embodiments in which the filter membrane is affixed by a ring that compresses the filter membrane edge onto the rim. The fifth embodiments can be modified to form additional fifth embodiments in which the inner wall has more than two minor ribs on an outside surface thereof and two major ribs, wider than the minor ribs, to which the filter membrane is adhesively bonded.

In one or more sixth embodiments, a cross flow filtration system has an apheresis machine with a blood pump and blood circuit connectable to a patient. A cross-flow filter module is connected to the blood circuit. The filter circuit has a retentate channel, a permeate channel, and a filter membrane. The filter membrane separates the retentate channel from the permeate channel and is arranged parallel to a direction of fluid flow through the retentate channel. The filter membrane has an array of tapered pores extending through the filter membrane. Each pore has a cross-width dimension that narrows from one of the retentate and permeate channels to the other of the retentate and permeate channels.

The sixth embodiments may include variations thereof in which the cross-width dimension of each pore narrows from the retentate channel to the permeate channel. The sixth embodiments may include variations thereof in which the cross-width dimension of each pore narrows from the permeate channel to the retentate channel. The sixth embodiments may include variations thereof in which the controller is configured to control the flow rates such that the rise in transmembrane pressure is less than or equal to 100 torr. The sixth embodiments may include variations thereof in which the controller is configured to control the flow rates such that the average flow rate through the pores of the filter membrane is less than a characteristic red blood cell passage rate for the filter membrane, the characteristic red blood cell passage rate being that attending a maximum flow rate of washed red blood cells, with a hematocrit between 10% and 50%, that is effective for continuously flowing with less than a 100 torr rise in transmembrane pressure over a four hour timeframe. The sixth embodiments may include variations thereof in which the controller is configured to control the flow rates such that the average flow rate through the pores of the filter membrane is less than 350 $s^{-1}$ for circular pores having a minimum diameter in a range of 5.5-7.5 µm. The sixth embodiments may include variations thereof in which the retentate channel has a height that tapers from a first height at an upstream end of the retentate channel to a second height at a downstream end of the retentate channel, the second height being less than the first height. The sixth embodiments may include variations thereof in which each pore has a minimum diameter in a range of 4-8 µm, inclusive. The sixth embodiments may include variations thereof in which each pore has an axially-extending portion with a constant diameter, a length of the constant-diameter axially-extending portion being less than 1 µm. The sixth embodiments may include variations thereof in which each pore has an axially-extending portion with a constant diameter, a length of the constant-diameter axially-extending portion being in a range of 1-10 µm. The sixth embodiments may include variations thereof in which each pore is linearly tapered at angle of 15-25° with respect to a corresponding axis thereof. The sixth embodiments may include variations thereof in which the filter membrane is formed of a polymer. The sixth embodiments may include variations thereof in which the polymer comprises polyimide, polyethylene terephthalate, or polycarbonate.

In one or more seventh embodiments, a cross flow filtration system has an apheresis machine with a blood pump and blood circuit connectable to a patient. A cross-flow filter module is connected to the blood circuit and has a retentate channel, a permeate channel, and a filter membrane. The filter membrane separates the retentate channel from the permeate channel and is arranged parallel to a direction of fluid flow through the retentate channel. The filter membrane has an array of pores extending through the filter membrane and between the permeate and retentate channels.

The seventh embodiments may include variations thereof in which the cross-width dimension of each pore narrows from the retentate channel to the permeate channel. The seventh embodiments may include variations thereof in which the cross-width dimension of each pore narrows from the permeate channel to the retentate channel. The seventh embodiments may include variations thereof that include a controller configured to control the flow rates such that a rise in transmembrane pressure is less than or equal to 100 torr.

The seventh embodiments may include variations thereof in which the controller is configured to control the flow rates such that the average flow rate through the pores of the filter membrane is less than a characteristic red blood cell passage rate for the filter membrane, the characteristic red blood cell passage rate being that attending a maximum flow rate of washed red blood cells, with a hematocrit between 10% and 50%, that is effective for continuously flowing with less than a 100 torr rise in transmembrane pressure over a four hour timeframe.

The seventh embodiments may include variations thereof in which the controller is configured to control the flow rates such that the average flow rate through the pores of the filter membrane is less than $350\ s^{-1}$ for circular pores having a minimum diameter in a range of 5.5-7.5 µm. The seventh embodiments may include variations thereof in which each pore has a minimum diameter in a range of 4-8 µm, inclusive. The seventh embodiments may include variations thereof in which each pore has an axially-extending portion with a constant diameter, a length of the constant-diameter axially-extending portion being less than 1 µm. The seventh embodiments may include variations thereof in which each pore has an axially-extending portion with a constant diameter, a length of the constant-diameter axially-extending portion being in a range of 1-10 µm. The seventh embodiments may include variations thereof in which each pore is linearly tapered at angle of 15-25° with respect to a corresponding axis thereof. The seventh embodiments may include variations thereof in which the filter membrane is formed of a polymer. The seventh embodiments may include variations thereof in which the polymer comprises polyimide, polyethylene terephthalate, or polycarbonate.

The seventh embodiments may include variations thereof in which the cross-flow filter module has a rigid cylindrical inner wall forming part of one of the retentate and permeate channels and a rigid cylindrical outer wall forming part of the other of the retentate and permeate channels. The seventh embodiments may include variations thereof in which the filter membrane of inelastic material. The seventh embodiments may include variations thereof in which the filter module has transition channels shaped and connected to the inner and outer walls to deliver a flow of fluid from an inlet port to the retentate channel and to capture flow flowing longitudinally along the cylindrical inner and outer walls from both the retentate and permeate channels to respective outlet ports. The seventh embodiments may include variations thereof in which the inner wall forms a part of the retentate channel and the outer wall forms a part of the permeate channel. The seventh embodiments may include variations thereof in which the inner wall has ribs that span a depth of the retentate channel. The seventh embodiments may include variations thereof in which the transition channels are spherical in shape. The seventh embodiments may include variations thereof in which the filter membrane is a polymer sheet with a regular array of pores extending through the filter membrane. The seventh embodiments may include variations thereof in which the filter membrane is formed by laser drilling the pores. The seventh embodiments may include variations thereof in which the filter membrane is a polyimide sheet with a regular array of tapered pores extending through the filter membrane.

The seventh embodiments may include variations thereof in which the filter membrane is a polyimide sheet with a regular array of rectangular pores extending through the filter membrane. The seventh embodiments may include variations thereof in which the filter membrane is a polyimide sheet with a regular array of rectangular pores extending through the filter membrane, the rectangular pores each having a long dimension and a short, wherein the long dimension of each pore is aligned with an axis of the outer wall. The seventh embodiments may include variations thereof in which the filter membrane is a polyimide sheet with a regular array of rectangular pores extending through the filter membrane, the rectangular pores each having a long dimension and a short, wherein the short dimension of each pore is aligned with an axis of the outer wall. The seventh embodiments may include variations thereof in which each pore has an axially-extending portion with a constant diameter, a length of the constant-diameter axially-extending portion being in a range of 1-10 µm. The seventh embodiments may include variations thereof in which each pore has a minimum diameter in a range of 4-8 µm, inclusive. The seventh embodiments may include variations thereof in which each pore has an axially-extending portion with a constant diameter, a length of the constant-diameter axially-extending portion being less than 1 µm.

The seventh embodiments may include variations thereof in which the ports are configured to withstand a pressure of at least 200 torr. The seventh embodiments may include variations thereof in which the transition channels each have a rim that supports an edge of the filter membrane. The seventh embodiments may include variations thereof in which the filter membrane is affixed by a ring that compresses the filter membrane edge onto the rim. The seventh embodiments may include variations thereof in which the inner wall has more than two minor ribs on an outside surface thereof and two major ribs, wider than the minor ribs, to which the filter membrane is bonded.

Any of the foregoing embodiments can be modified such that the pore spacing and size are such that the open area in terms of a percentage of face are of the filter membrane is between 5 and 15 percent. Any of the foregoing embodiments can be modified such that the pore spacing and size are such that the open area in terms of a percentage of face are of the filter membrane is between 8 and 12 percent. Any of the foregoing embodiments can be modified such that the pore spacing and size are such that the open area in terms of a percentage of face are of the filter membrane is between 9 and 11 percent.

Furthermore, the foregoing descriptions apply, in some cases, to examples generated in a laboratory, but these examples can be extended to production techniques. For example, where quantities and techniques apply to the laboratory examples, they should not be understood as limiting. In addition, although specific chemicals and materials have been disclosed herein, other chemicals and materials may also be employed according to one or more contemplated embodiments.

In this application, unless specifically stated otherwise, the use of the singular includes the plural and the use of "or" means "and/or." Furthermore, use of the terms "including" or "having," as well as other forms, such as "includes," "included," "has," or "had" is not limiting. Any range described herein will be understood to include the endpoints and all values between the endpoints.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, system, methods, and devices for removing circulating tumor cells from blood. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A method of removing circulating tumor cells (CTCs) from whole blood, the method comprising:
   for a first duration, continuously flowing and recirculating whole blood along and parallel to a first side of a filter membrane while withdrawing filtrate that has passed through to a second side of the filter membrane opposite the first side such that red blood cells from the whole blood pass through the filter membrane without a rise in transmembrane pressure exceeding 100 torr over the first duration
   wherein the filter membrane has an array of pores, each pore tapering with respect to a thickness direction of the filter membrane from one of the first and second sides to the other of the first and second sides, and
   said one of the first and second sides has a greater open area than said other of the first and second sides of the filter membrane.

2. The method of claim 1, wherein each pore tapers with respect to the thickness direction from the first side to the second side such that the first side has a greater open area than the second side of the filter membrane.

3. The method of claim 1, wherein each pore tapers with respect to the thickness direction from the second side to the first side such that the second side has a greater open area than the first side of the filter membrane.

4. The method of claim 1, wherein the array of pores are sized so as to obstruct passage of CTCs therethrough.

5. The method of claim 1, wherein the continuously flowing whole blood and withdrawing filtrate are such that an average shear rate through the pores of the filter membrane is less than 350 s−1 for circular pores having a minimum diameter in a range of 5.5-7.5 μm.

6. The method of claim 1, wherein the continuously flowing whole blood and withdrawing filtrate are such that a shear rate at each point across the first side of the filter membrane is between 500 s−1 and 1000 s−1.

7. The method of claim 1, wherein the continuously flowing whole blood and withdrawing filtrate are such that shear rate at each point across the first side of the filter membrane is greater than an average shear rate through the pores of the filter membrane.

8. The method of claim 1, wherein the continuously flowing and recirculating is of a volume of 20 ml to 500 ml.

9. The method of claim 1, further comprising:
   collecting retentate that has not passed through the filter membrane.

10. The method of claim 1, further comprising:
    withdrawing the whole blood from a patient during the continuously flowing and recirculating; and
    injecting the filtrate into the patient.

11. The method of claim 10, wherein
the first duration is at least one hour.

12. The method of claim 10, wherein
the withdrawing the filtrate that has passed through to the second side of the filter membrane is at a flow rate of 5-80 ml/min.

13. The method of claim 10, wherein
the injecting the filtrate into the patient is at a flow rate of 100 ml/min.

14. The method of claim 10, wherein
recirculation of the whole blood along and parallel to the first side of the filter membrane is at a flow rate of 1-10 ml/min.

15. The method of claim 1, wherein
the first duration is at least one hour.

16. The method of claim 1, wherein
the first duration is between 1 and 4 hours.

17. The method of claim 1, wherein
the continuously flowing and recirculating is of a volume between 4 and 6 liters.

18. The method of claim 1, wherein
the continuously flowing and recirculating is of a volume between 8 and 18 liters.

19. The method of claim 1, wherein
the withdrawing the filtrate that has passed through to the second side of the filter membrane is at a flow rate of 5-80 ml/min.

* * * * *